(12) United States Patent
Kuwabara et al.

(10) Patent No.: US 10,881,315 B2
(45) Date of Patent: Jan. 5, 2021

(54) BIOLOGICAL SIGNAL MEASUREMENT SYSTEM, BIOLOGICAL INFORMATION MEASUREMENT APPARATUS, AND BIOLOGICAL INFORMATION EXTRACTION ALGORITHM CHANGING METHOD

(71) Applicant: NIPPON TELEGRAPH AND TELEPHONE CORPORATION, Tokyo (JP)

(72) Inventors: Kei Kuwabara, Tokyo (JP); Takayuki Ogasawara, Tokyo (JP); Nobuaki Matsuura, Tokyo (JP); Michiko Seyama, Tokyo (JP); Hiroshi Koizumi, Tokyo (JP); Ryusuke Kawano, Tokyo (JP); Kazuhiko Takagahara, Tokyo (JP); Kazuyoshi Ono, Tokyo (JP); Takako Ishihara, Tokyo (JP); Yasuhiro Sato, Tokyo (JP); Shingo Tsukada, Tokyo (JP); Nahoko Kasai, Tokyo (JP); Koji Sumitomo, Tokyo (JP)

(73) Assignee: NIPPON TELEGRAPH AND TELEPHONE CORPORATION, Tokyo (JP)

( * ) Notice: Subject to any disclaimer, the term of this patent is extended or adjusted under 35 U.S.C. 154(b) by 0 days.

(21) Appl. No.: 15/502,995

(22) PCT Filed: Aug. 4, 2015

(86) PCT No.: PCT/JP2015/072060
§ 371 (c)(1),
(2) Date: Feb. 9, 2017

(87) PCT Pub. No.: WO2016/024495
PCT Pub. Date: Feb. 18, 2016

(65) Prior Publication Data
US 2017/0224244 A1   Aug. 10, 2017

(30) Foreign Application Priority Data

Aug. 11, 2014 (JP) .................................. 2014-163402
Nov. 12, 2014 (JP) .................................. 2014-229773

(51) Int. Cl.
*A61B 5/0456* (2006.01)
*A61B 5/0452* (2006.01)
(Continued)

(52) U.S. Cl.
CPC .......... *A61B 5/0456* (2013.01); *A61B 5/0006* (2013.01); *A61B 5/0022* (2013.01);
(Continued)

(58) Field of Classification Search
CPC ....... A61B 5/04; A61B 5/0412; A61B 5/0456; A61B 5/0452; A61B 5/7285; A61B 2560/0223; A61N 1/36031; A61N 1/37252
See application file for complete search history.

(56) References Cited

U.S. PATENT DOCUMENTS 7,187,965 B2 * 3/2007 Bischoff ............ A61B 5/02405
600/515
2003/0204140 A1 * 10/2003 Ferek-Patric ...... A61N 1/36528
600/439
(Continued)

FOREIGN PATENT DOCUMENTS

CN  101019761 A  8/2007
CN  102008300 A  4/2011
(Continued)

OTHER PUBLICATIONS

David M. D. Ribeiro, et. al., "A Real time, Wearable ECG and Continuous Blood Pressure Monitoring System for First Responders," 33rd Annual International Conference of the IEEE EMBS, pp. 6894-6898, 2011.
(Continued)

*Primary Examiner* — Alyssa M Alter
(74) *Attorney, Agent, or Firm* — Womble Bond Dickinson (US) LLP

(57) ABSTRACT

In a biological signal measurement system of this invention, biological digital data is generated from a biological signal measured by a biological signal measurement apparatus, and
(Continued)

first feature amount data extracted from the biological digital data and downsized biological digital data are transmitted to a portable terminal. In a biological information measurement apparatus of this invention, biological feature amount data is extracted from measured biological waveform data, and at least one of the biological waveform data and the biological feature amount data is transmitted to an external device. It is possible to provide a biological signal measurement system capable of continuously measuring a biological signal for a long time without disturbing daily life and provide a biological information measurement apparatus capable of implementing downsizing and long life of a battery.

15 Claims, 13 Drawing Sheets

(51) Int. Cl.
    *A61B 5/0404*     (2006.01)
    *A61B 5/0428*     (2006.01)
    *A61B 5/00*     (2006.01)
    *A61B 5/0205*     (2006.01)
    *A61B 5/04*     (2006.01)
    *A61B 5/0408*     (2006.01)

(52) U.S. Cl.
    CPC ........ *A61B 5/02055* (2013.01); *A61B 5/0404* (2013.01); *A61B 5/04012* (2013.01); *A61B 5/0428* (2013.01); *A61B 5/0452* (2013.01); *A61B 5/04085* (2013.01); *A61B 5/6804* (2013.01); *A61B 5/6831* (2013.01); *A61B 2560/0209* (2013.01); *A61B 2560/0214* (2013.01); *A61B 2560/0242* (2013.01)

(56) References Cited

U.S. PATENT DOCUMENTS

| | | |
|---|---|---|
| 2006/0025697 A1 | 2/2006 | Kurzweil et al. |
| 2008/0140159 A1 | 6/2008 | Bornhoft et al. |
| 2011/0066053 A1 | 3/2011 | Yazicioglu |
| 2012/0172689 A1 | 7/2012 | Albert et al. |
| 2012/0257698 A1 | 10/2012 | Zhang |
| 2012/0262303 A1* | 10/2012 | Fahey ................. A61B 5/0006 340/870.02 |
| 2013/0197380 A1 | 8/2013 | Oral et al. |
| 2013/0218030 A1 | 8/2013 | Barroso et al. |
| 2013/0289424 A1 | 10/2013 | Brockway et al. |
| 2014/0320307 A1* | 10/2014 | Matsuno ............. A61B 5/0002 340/870.07 |

FOREIGN PATENT DOCUMENTS

| | | |
|---|---|---|
| CN | 103598884 A | 2/2014 |
| CN | 103635130 A | 3/2014 |
| CN | 103635430 A | 3/2014 |
| EP | 2447866 A1 | 5/2012 |
| JP | 2007-075372 A | 3/2007 |
| JP | 2011-519583 A | 7/2011 |
| JP | 2014-510545 A | 5/2014 |
| JP | 2014-124345 A | 7/2014 |
| WO | WO 2009/112976 A1 | 9/2009 |
| WO | WO 2012/056342 A2 | 5/2012 |
| WO | 2012/142462 A1 | 10/2012 |

OTHER PUBLICATIONS

Ali Moti Nasrabadi et. al., "Design of ECG acquisition and transmission via Bluetooth with heart disease diagnosis," IEEE International Workshop on Medical Measurements and Applications Proceedings, pp. 55-58, 2011.
Supplementary Partial European Search Report and Written Opinion received for EP Patent Application No. 15832088.7, dated Mar. 1, 2018, 17 pages.
International Search Report and Written Opinion received for PCT Patent Application No. PCT/JP2015/072060, dated Nov. 2, 2015, 20 pages (10 pages of English Translation and 10 pages of Original Document).
International Preliminary Report on Patentability received for PCT Patent Application No. PCT/JP2015/072060, dated Feb. 23, 2017, 14 pages (9 pages of English Translation and 5 pages of Original Document).
Office Action with Search Report dated May 2, 2017, TW Application No. 104125960.
Office Action with Search Report dated Jan. 17, 2017, TW Application No. 104125960.
Office Action received for European Patent Application No. 15832088.7, dated Apr. 17, 2019, 5 pages.
Office Action received for Chinese Patent Application No. 201580043054.9, dated Mar. 8, 2019, 17 pages (8 pages of English Translation and 9 pages of Office Action).
"European Extended Search Report," EP Application No. 15832088.7 (dated Jul. 4, 2018).
Office Action received for European Patent Application No. 15832088.7, dated Nov. 15, 2019, 8 pages.
Office Action received for Chinese Patent Application No. 201580043054.9, dated Apr. 21, 2020, 24 pages (13 pages of English Translation and 11 pages of Office Action).

\* cited by examiner

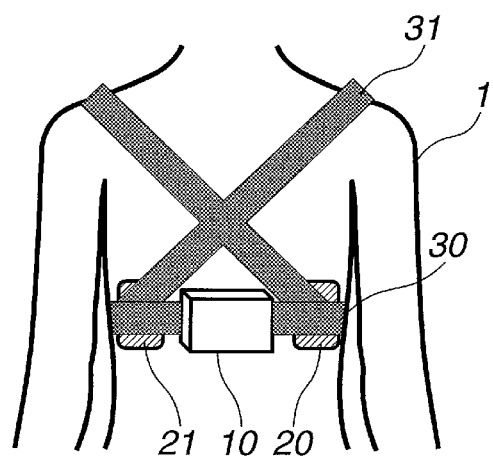
FIG.3A
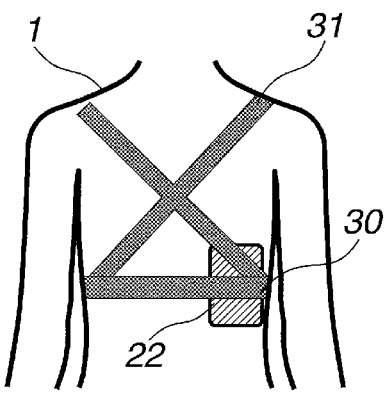
FIG.3B
FIG.4A
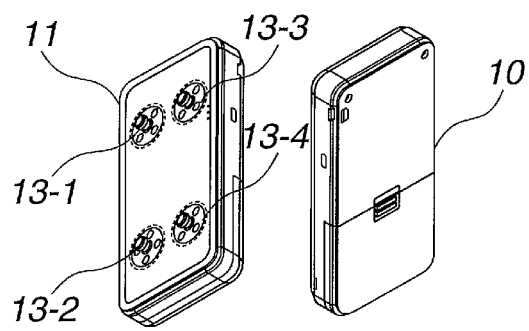

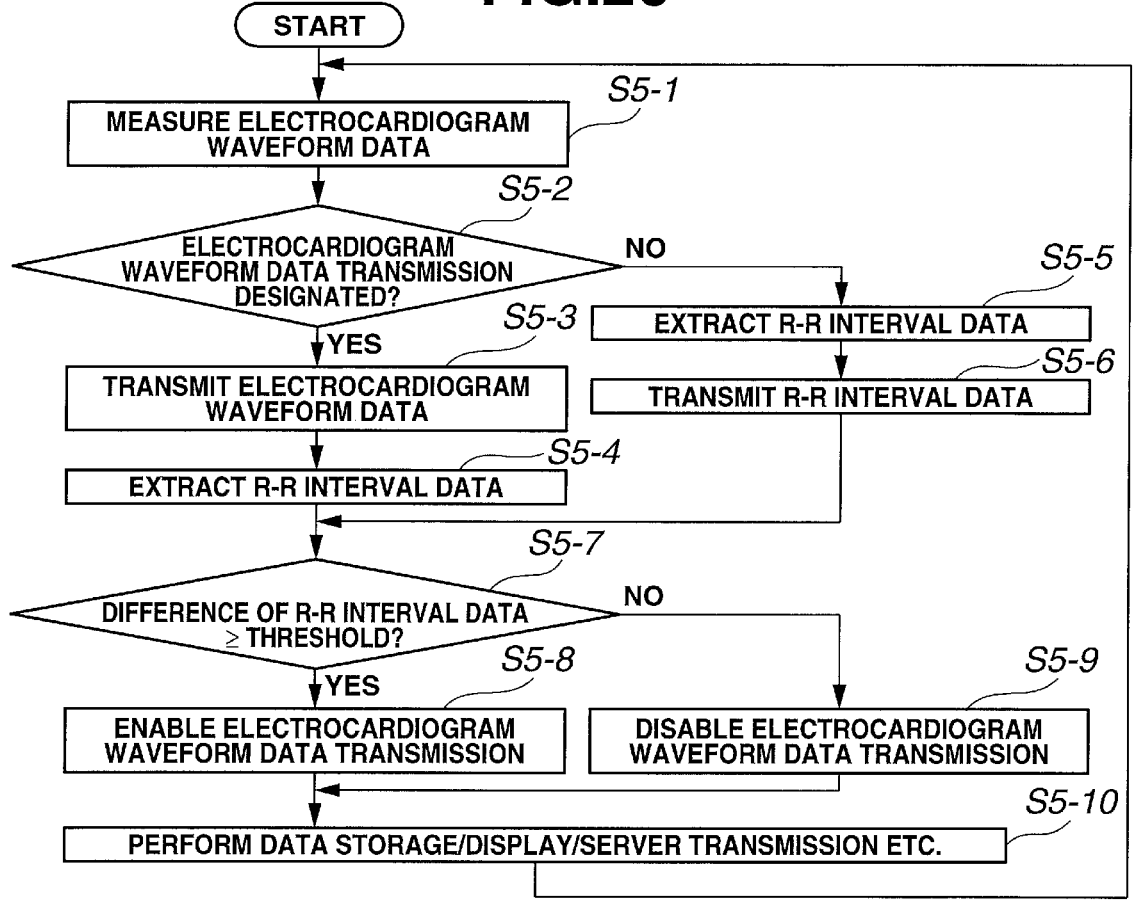
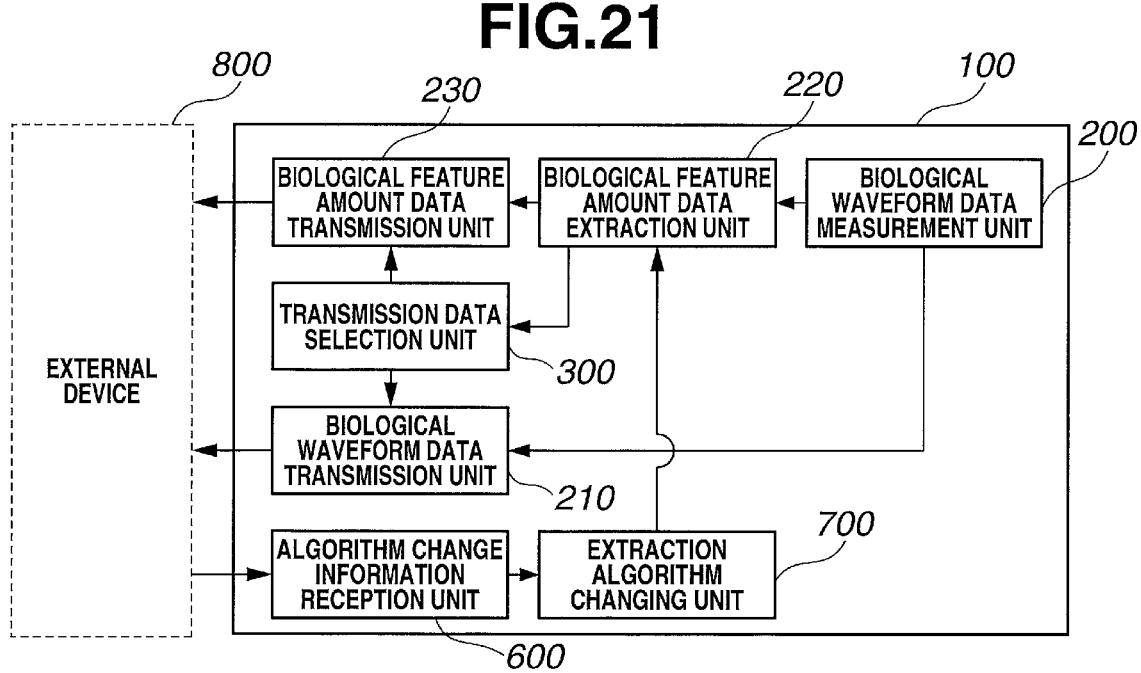

BIOLOGICAL SIGNAL MEASUREMENT SYSTEM, BIOLOGICAL INFORMATION MEASUREMENT APPARATUS, AND BIOLOGICAL INFORMATION EXTRACTION ALGORITHM CHANGING METHOD

TECHNICAL FIELD

The present invention relates to a biological signal measurement system for measuring a biological signal including an electrocardiogram signal.

BACKGROUND ART

Along with a recently growing interest in health, a health care method has started becoming widespread, which records and analyzes biological information for a long time of several hours to several months or more, thereby monitoring physical and mental states in daily life. As a method of acquiring biological information for a long time, clothing (wearable electrode) with biological electrodes has received attention (for example, see non-patent literatures 1 and 2).

Examples of biological information to be acquired are a heart rate, R-R interval, electrocardiogram waveform, number of steps, active mass, and body acceleration. Using these pieces of biological information monitored every day, the life style can be improved for health promotion, or a disease can early be detected.

A biological signal detected by biological electrodes is accumulated in an apparatus electrically connected to the biological electrodes. When the biological signal is transmitted to an external personal computer or the like using a communication function, the data can be analyzed in real time. To implement the long-time monitoring in daily life, the apparatus for measuring the biological signal needs to be compact and wearable and have a low power consumption so that it can be driven by a battery for a long time.

In addition, the recent proliferation of smartphones and the like makes it possible to always carry a high-performance processor and a large-capacity memory. This enables a method of transmitting measured biological information to an external device such as a smartphone and executing analysis and accumulation of data, thereby reducing the load on the apparatus for measuring the biological information and implementing downsizing and a long-time operation (for example, see non-patent literature 2).

Of above-described biological information, the electrocardiogram waveform can be classified into biological waveform data that can directly be measured by reading the voltage of biological electrodes attached to a living body and performing amplification and frequency filtering as needed.

On the other hand, the heart rate and heartbeat fluctuation can be classified into biological feature amount data that can be acquired by analyzing the feature amount of an electrocardiogram waveform. The R-R interval is feature amount data obtained by detecting R waves from an electrocardiogram waveform and measuring the time between adjacent R waves. The heart rate is feature amount data that can be obtained by averaging the reciprocals of the R-R intervals.

Similarly, the body acceleration is biological waveform data that can be obtained from an acceleration sensor attached to a living body. The number of steps and the active mass are biological feature amount data that can be acquired by analyzing the body acceleration. Normally, the biological feature amount data is obtained by extracting the feature of part of biological waveform data and therefore has a small data amount as compared to the biological waveform data.

Conventional biological information measurement apparatuses include an apparatus of a biological waveform data transmission type that, as shown in FIG. 23A, measures biological waveform data by a biological waveform data measurement unit 200 and transmits it to an external device 800 by a biological waveform data transmission unit 210, and an apparatus of a biological feature amount data transmission type that, as shown in FIG. 23B, measures biological waveform data by the biological waveform data measurement unit 200, after that, extracts biological feature amount data by a biological feature amount data extraction unit 220 in a biological information measurement apparatus 100, and transmits it to the external device 800 by a biological feature amount data transmission unit 230.

The biological waveform data type can transfer more abundant information to the external device 800. In addition, since biological feature amount data is extracted from received biological waveform data on the side of the external device 800 having a processing capability more advanced than that of the biological information measurement apparatus, the external device extraction accuracy can be improved. On the other hand, the biological feature amount data transmission type can decrease the amount of data transmitted to the external device 800 and is therefore suitable for reduction of power consumption and downsizing of a battery.

RELATED ART LITERATURE

Patent Literature

Non-Patent Literature 1: David M. D. Ribeiro, et. al., "A Real time, Wearable ECG and Continuous Blood Pressure Monitoring System for First Responders," 33rd Annual International Conference of the IEEE EMBS, pp. 6894-6898, 2011.

Non-Patent Literature 2: Ali Moti Nasrabadi et. al., "Design of ECG acquisition and transmission via Bluetooth with heart disease diagnosis," IEEE International Workshop on Medical Measurements and Applications Proceedings, pp. 55-58, 2011.

DISCLOSURE OF INVENTION

Problem to be Solved by the Invention

To acquire an accurate electrocardiogram waveform of medical level or extract feature amount data, sampling at a high sampling rate of 125 Hz to 1,000 Hz is necessary. If the sampling rate is high, an acquired data amount is also large. Hence, to analyze a biological signal in real time, the biological signal measurement apparatus needs to transmit a large amount of data for a long time.

On the other hand, an electronic circuit or a wireless module included in the biological signal measurement apparatus can be formed very small. However, the capacity of a battery that drives the apparatus is in proportion to the size of the battery. To ensure a battery capacity to transmit a large amount of data for a long time, the size of the terminal needs to be large. To continuously measure a biological signal for a long time without disturbing the daily life, it is necessary to reduce the size and power consumption of the biological signal measurement apparatus and drive the apparatus for a long time by a battery.

As described above, to do real-time measurement of a biological signal for a long time without disturbing the daily life, acquisition of an accurate biological signal of medical level and reduction of the size and power consumption of the biological signal measurement apparatus need to be implemented simultaneously.

In addition, the above-described conventional biological information measurement apparatus of the biological waveform data transmission type needs to transmit biological waveform data with a large information amount to an external device. For this reason, power consumption necessary for communication and the like is high, and it is difficult to make the battery compact and long-lived. On the other hand, in the conventional biological information measurement apparatus of the biological feature amount data transmission type, information other than the extracted feature amount is lost, and the biological feature amount is extracted using the information processing capability lower than that of the external device, an extraction failure or an extraction error of a biological feature amount data occurs.

It is an object of the present invention to provide a biological information measurement apparatus capable of suppressing the communication amount of the biological information measurement apparatus and implementing downsizing and long life of a battery and also capable of reducing an extraction failure or an extraction error of a biological feature amount data.

Means of Solution to the Problem

According to the present invention, there is provided a biological signal measurement system comprising biological electrodes capable of coming into contact with a surface of a living body, and a biological signal measurement apparatus comprising means for generating first biological digital data by quantizing, based on a first sampling rate, a biological electrical signal detected by the biological electrodes, means for extracting first feature amount data from the first biological digital data, means for generating second biological digital data downsized from the first biological digital data to a data size corresponding to a second sampling rate lower than the first sampling rate, and wireless communication means for transmitting the second biological digital data and the first feature amount data to a portable terminal.

According to the present invention, there is also provided a biological signal measurement system comprising biological electrodes capable of coming into contact with a surface of a living body, and a biological signal measurement apparatus comprising means for generating first biological digital data by quantizing, based on a first sampling rate, a biological electrical signal detected by the biological electrodes, means for extracting first feature amount data from the first biological digital data, means for generating second biological digital data downsized from the first biological digital data to a data size corresponding to a second sampling rate lower than the first sampling rate, wireless communication means for transmitting at least one of the second biological digital data and the first feature amount data to a portable terminal, transmission data designation information reception means for receiving transmission data designation information that designates data to be transmitted by the wireless communication means, and transmission data selection means for selecting, based on the transmission data designation information, the data to be transmitted by the wireless communication means.

According to the present invention, there is also provided a biological information measurement apparatus comprising biological waveform data measurement means for measuring biological waveform data, feature amount data extraction means for extracting biological feature amount data from the biological waveform data in accordance with a predetermined extraction algorithm, data transmission means for transmitting at least one of the biological waveform data and the biological feature amount data, and transmission data selection means for selecting data to be transmitted by the transmission means, wherein different data transmission intervals are used to transmit the biological waveform data and the biological feature amount data.

According to the present invention, there is also provided a biological information extraction algorithm changing method comprising the steps of measuring biological waveform data, extracting biological feature amount data from the biological waveform data in accordance with a predetermined extraction algorithm, evaluating reliability of the biological feature amount data, analyzing the biological waveform data if the reliability is lower than a predetermined reference value, and changing the predetermined algorithm based on an analysis result of the biological waveform data.

Effect of the Invention

According to the present invention, it is possible to provide a biological signal measurement system that optimizes processing division and the data transfer amount between the apparatuses that constitute the system of measuring biological information, thereby simultaneously implementing acquisition of an accurate biological signal of medical level and reduction of the size and power consumption of the biological signal measurement apparatus and browsing and analyzing a biological signal in real time.

Additionally, it is possible to select whether to transmit one or both of biological waveform data and biological feature amount data. Hence, if biological waveform data is unnecessary, only biological feature amount data is transmitted, thereby suppressing the communication amount and implementing downsizing and long life of a battery.

BRIEF DESCRIPTION OF DRAWINGS

FIG. 3A is a view showing an example (front view) of a structure that brings the biological electrodes into contact with the living body using a belt-shaped structure and a cross brace-shaped structure;

FIG. 3B is a view showing an example (rear view) of the structure that brings the biological electrodes into contact with the living body using the belt-shaped structure and the cross brace-shaped structure;

FIG. 4A is a view showing an example of the outer shape of a biological signal measurement apparatus according to the first embodiment of the present invention;

FIG. 20 is a flowchart for explaining the procedure of biological information measurement in a case in which data to be transmitted is selected based on the reliability of feature amount data;

FIG. 21 is a functional block diagram of a biological information measurement apparatus according to the sixth embodiment of the present invention;

BEST MODE FOR CARRYING OUT THE INVENTION

The best mode for carrying out the present invention will now be described with reference to the accompanying drawings. The present invention is not limited by the following embodiments.

First Embodiment

A biological signal measurement system according to the first embodiment will be described below.

Figure 1:
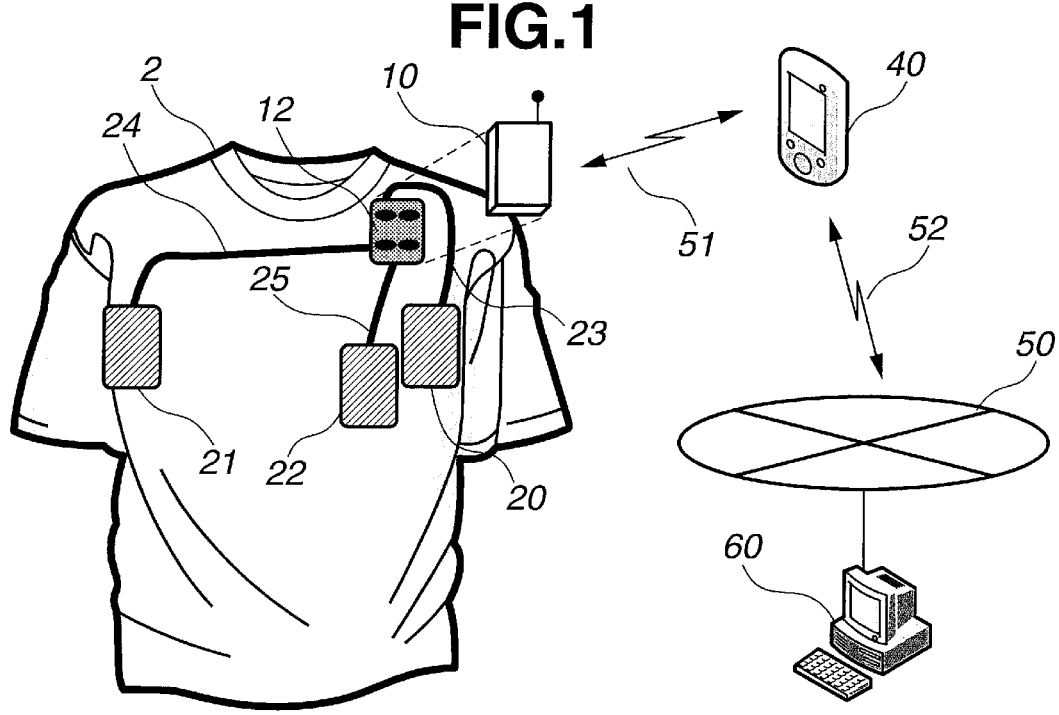
FIG. 1 is a view showing the basic arrangement of a biological signal measurement system according to the first embodiment of the present invention.

The biological signal measurement system shown in FIG. 1 is formed from clothing 2 including at least two biological electrodes (20 to 22) made of a conductive fiber structure and capable of contacting the skin of a living body, a biological signal measurement apparatus 10 easily detachable from the clothing 2, and a portable terminal 40 represented by a smartphone capable of connecting with the biological signal measurement apparatus 10 by wireless communication and capable of connecting with a public network. The biological electrodes and the biological signal measurement apparatus are electrically connected via wires (23 to 25).

The biological signal measurement apparatus 10 executes amplification, quantization (analog-to-digital conversion), and the like for biological signals detected from the biological electrodes (20 to 22) to generate biological digital data, analyzes the biological digital data, performs filtering or the like to extract feature amount data, and transmits the feature amount data to the portable terminal 40 by wireless communication. The portable terminal 40 displays the received biological digital data as a graph or further analyzes the biological digital data or received feature amount data to generate another feature amount data. The biological signal measurement apparatus 10 may store the biological digital data or feature amount data. However, the biological signal measurement apparatus 10 may transfer the data to the portable terminal 40 and then discard the data.

The biological signal measurement system according to the present invention includes the clothing 2 on which the biological electrodes (20 to 22) made of a fiber structure with electric conductivity, such as a conductive fabric are arranged at positions suitable for detection of a biological signal such as an electrocardiogram signal. The arrangement shown in FIG. 1 is a three-electrode configuration in which two electrodes are arranged near the armpits such that the positive electrode 20 is located on the left hand side, and the negative electrode 21 is located on the right hand side, and the indifferent electrode 22 (a GND electrode or a biological reference potential electrode) is separately arranged under the positive electrode. Positions for a substantial CC5 lead are exemplified. All the biological electrodes (20 to 22) are fixed inside the clothing 2 that is in direct contact with the living body.

The CC5 lead is approximate to a V4 of V5 lead in 12-lead electrocardiogram and can largely detect the amplitude of a QRS signal in an electrocardiogram signal. Hence, the CC5 lead is suitable to extract feature amount data such as a pulse period (R-R interval) by automatic analysis. However, the positions of the biological electrodes are not limited to the illustrated lead positions. Not a bipolar lead such as the CC5 lead but a unipolar lead may be used, and arranging at least two biological electrodes separately suffices.

The wires (23 to 25) made of a material with electric conductivity are connected to the biological electrodes (20 to 22). The wires are further connected to a terminal connector 12 used to connect the biological signal measurement apparatus 10. At this time, the biological electrodes are insulated from each other. The biological electrodes (20 to 22) and the wires (23 to 25) need to be selected not to cause an electromotive force (polarization) or corrosion by the connection. The terminal connector 12 is preferably formed from a conductive member that can easily detach the biological signal measurement apparatus 10 and has a resistance to washing.

As described above, the biological signal measurement apparatus 10 according to this embodiment has a connection function of enabling detachment from the clothing 2 and establishment of electrical conduction with the biological electrodes (20 to 22) provided on the clothing 2, a signal processing function of amplifying a biological electrical signal detected by each of the biological electrodes (20 to 22) and quantizing the biological signal, a signal analysis function of analyzing the biological signal and extracting feature amount data, and a wireless communication function of wirelessly connecting the portable terminal 40.

A weak biological signal obtained by the connection function is generally several mV or less even in an electrocardiogram signal. Hence, the signal is amplified to a predetermined signal level by the signal processing function. Additionally, unnecessary noise and fluctuation are filtered, and quantization is performed by analog-to-digital conversion, thereby generating biological digital data. Furthermore, necessary filtering is performed by the signal analysis function to extract feature amount data.

The wireless communication function provides a communication function with the portable terminal, transmits obtained biological digital data or feature amount data obtained by signal analysis, or receives a signal for necessary remote control from the portable terminal. In this embodiment, connection with the portable terminal is done using a low-power radio 51 such as Bluetooth® from the viewpoint of power consumption reduction. The biological signal measurement apparatus may have a memory function of storing obtained data.

The portable terminal 40 represented by a smartphone is not only connected to the biological signal measurement apparatus 10 by the low-power radio 51 such as Bluetooth but also connected to a public network 50 (Internet) by a cellular method or a wireless LAN method 52. The portable terminal 40 can display biological information such as electrocardiogram signal data or feature amount data obtained from the biological signal measurement apparatus 10, perform data analysis, conversion, processing, or the like to obtain necessary information, analyze the electrocardiogram signal data, and generate another feature amount data.

The portable terminal 40 can also transmit these pieces of biological information to a cloud server 60 via the public network 50 together with identification information (for example, the sex, age, height/weight, and the like of an individual) or the position information of the portable terminal. Data from the biological signal measurement apparatus 10 may be transmitted to the cloud server 60 in real time like a bucket brigade. However, an arbitrary amount of data may be put together in a file and transmitted.

The cloud server 60 can perform statistical analysis (for example, analysis by sex or age, analysis by a physical characteristic of an individual, or analysis by a location) for the transmitted biological information of a plurality of individuals using identification information and the like and feed back the analysis result to the portable terminal 40. This makes it possible to not only continuously acquire a biological signal such as an electrocardiogram signal and analyze it without disturbing the daily life but also perform statistical analysis called big data analysis based on a plurality of personal data and obtain valuable information that is impossible conventionally. Note that the identification information is stored in one of the biological signal measurement apparatus 10 and the portable terminal 40 and transmitted to the cloud server as needed.

In this embodiment, the clothing 2 on which the biological electrodes (20 to 22) are placed represents underwear. However, clothing such as sportswear positively exposed to public may be used. In any case, the electrodes made of a fabric having conductivity are fixed inside the clothing in direct contact with the living body.

As the electrode fabric with conductivity, a fabric containing PECOT-PSS polymer is appropriate because of its excellent biocompatibility. However, any fabric with conductivity, such as a silver-coated fabric, is usable. The electrodes (20 to 22) are connected to the terminal connector 12 using metal snap buttons by the wires (23 to 25) such as a silver thread. The silver thread may be a silver-plated thread formed by plating the surface of a nylon or polyester fiber with silver.

Figure 2A:
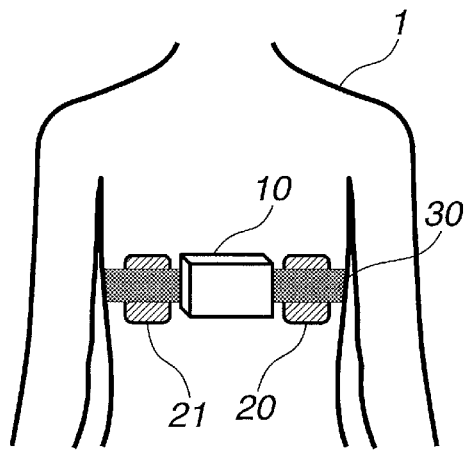
FIG. 2A is a view showing an example (front view) of a structure that brings biological electrodes into contact with a living body using a belt-shaped structure.
Figure 2B:
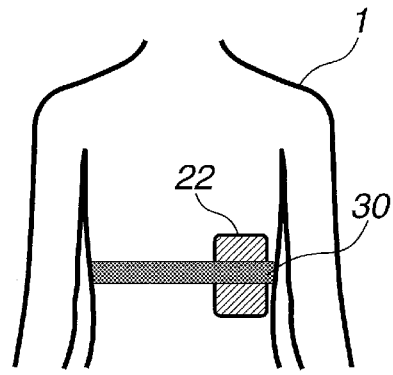
FIG. 2B is a view showing an example (rear view) of the structure that brings the biological electrodes into contact with the living body using the belt-shaped structure.

The electrode arrangement has been described with reference to FIG. 1 assuming a case in which the electrodes are arranged on clothing. However, the structure to arrange the electrodes is not limited to this. In FIGS. 2A and 2B, the electrodes are arranged using a belt-shaped structure other than clothing. In FIGS. 3A and 3B, the electrodes are arranged using a belt-shaped structure and a cross brace-shaped structure. A case in which all electrodes are fixed inside a structure that is in direct contact with a living body 1, and the positive electrode 20, the negative electrode 21, and the indifferent electrode 22 are placed is shown. Although the wires are not illustrated, they only need to be placed inside a belt-shaped structure 30 and a cross brace-shaped structure 31. The indifferent electrode 22 only needs to be located at a position part from the positive electrode 20 and the negative electrode 21. The indifferent electrode 22 need not always be placed. However, a variety of noise is known to be generated in measurement concerning a human body. To maintain higher noise immunity, the indifferent electrode 22 is preferably placed.

Figure 4B:
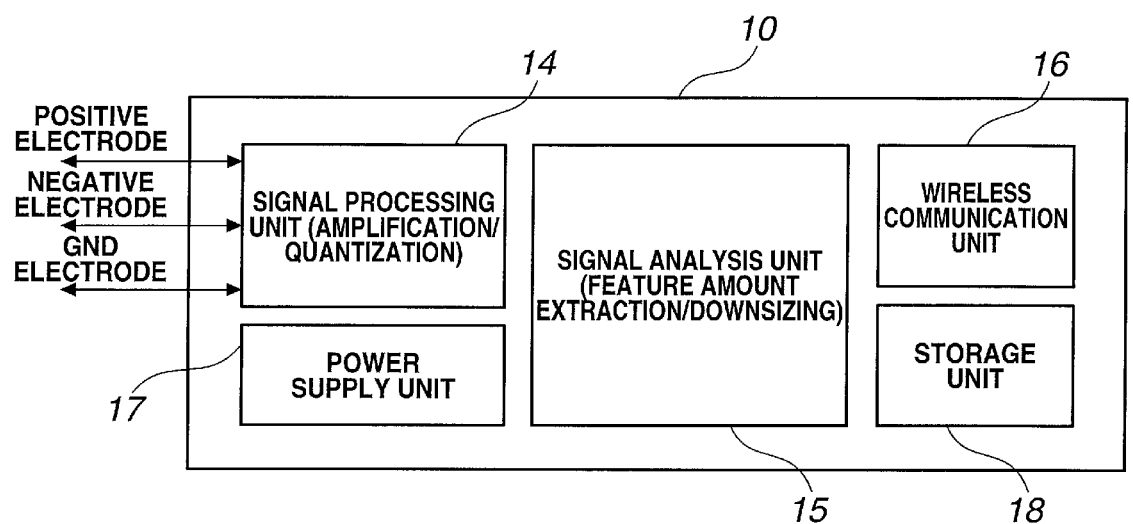
FIG. 4B is a functional block diagram of the biological signal measurement apparatus according to the first embodiment of the present invention.

In an example of the biological signal measurement apparatus shown in FIG. 4A, snap buttons 13-1 to 13-4 are arranged on a side 11 of the biological signal measurement apparatus 10 connected to the terminal connector 12. In FIG. 4A, the convex side is provided on the biological signal measurement apparatus side 11. However, the convex side may be provided on the terminal connector side, and the concave side may be provided on the biological signal measurement apparatus side. In the functional block diagram of FIG. 4B, the biological signal measurement apparatus 10 is driven by an internal power source. The voltage is preferably regulated to a necessary power supply voltage by a power supply unit 17 and thus stabilized for use.

A signal processing unit 14 differentially amplifies biological signals such as electrocardiogram signals input from the positive electrode and the negative electrode based on the indifferent electrode potential serving as a reference. Together with the amplification, filtering processing for noise removal and baseline stabilization is performed. Furthermore, quantization is performed by analog-to-digital conversion, and biological digital data such as quantized electrocardiogram signal data is generated. The biological digital data may further be shaped into a waveform easy to analyze by digital filtering. The amplification is generally performed by an instrumentation amplifier.

A signal analysis unit 15 extracts feature amount data such as a heart rate or R-R interval from biological digital data such as electrocardiogram signal data by signal processing, and also downsize the biological digital data in accordance with the communication capacity to the portable terminal 40. A wireless communication unit 16 wirelessly transmits the obtained biological digital data or obtained feature amount data to the portable terminal 40. The radio system used to connect the portable terminal 40 is preferably a low-power radio specialized to short-range communication such as Bluetooth from the viewpoint of power consumption reduction. The portable terminal 40 also has the same radio system.

Figure 5:
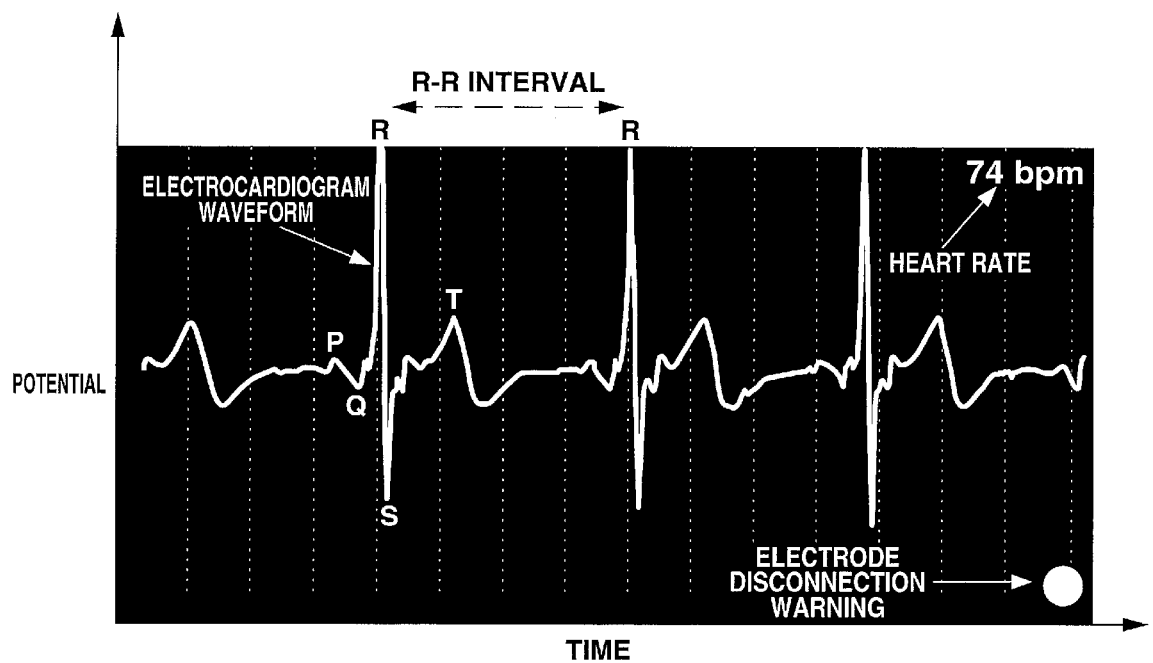
FIG. 5 is a graph showing an example of measurement of an electrocardiogram signal that is an example of a biological signal and an R-R interval that is an example of feature amount data.

The biological signal and the feature amount data to be extracted in this embodiment will be described. The following description will be made using an electrocardiogram signal as the biological signal. However, the present invention is not limited to this. In the example shown in FIG. 5, the electrocardiogram signal is formed from components such as a P-QRS-T wave reflecting the activity of an atrium or a ventricle. The time interval between adjacent R waves is feature amount data called an R-R interval. The reciprocal of the R-R interval is the heart rate. In the portable terminal 40 shown in FIG. 1, electrocardiogram signal data received from the biological signal measurement apparatus is displayed and stored as a file. Additionally, the contact state between the electrodes and the living body is monitored based on the level of impedance. If the contact state degrades due to, for example, separation of the electrodes from the living body, an electrode disconnection warning can be displayed to show the reason of a degradation of the electrocardiogram signal.

Figure 6A:
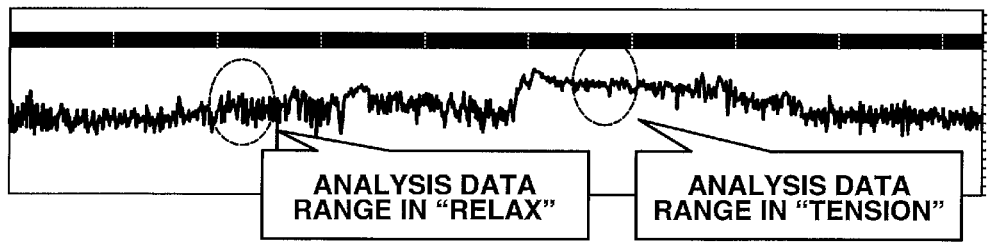
FIG. 6A is a graph showing an example of measurement of a tachogram of a heart rate.
Figure 6B:
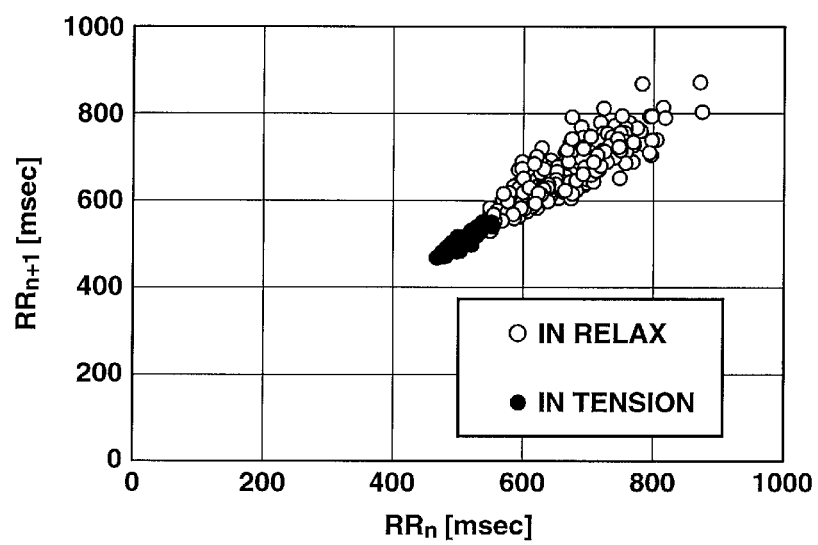
FIG. 6B is a graph showing an example of measurement of the Poincare plot of the R-R interval of an electrocardiogram signal.

When statistical analysis is further performed for the feature amount data such as the R-R interval extracted from the electrocardiogram signal data, another feature amount data can be generated. In a Poincare plot shown in FIG. 6B, R-R(n) that is an R-R interval at a certain time and R-R(n+1) that is the next R-R interval are plotted along the x- and y-coordinates, respectively, within the analysis data range of the measurement example of a tachogram of the heart rate shown in FIG. 6A. If R-R(n) and R-R(n+1) are approximate, the plots concentrate to one point. However, if the variation is large, the plots disperse. In general, tension is considered to lead to a small variation, and relaxation is considered to lead to a large variation.

As another example, as autonomic activity analysis using R-R intervals, CVRR (Coefficient of Variation of R-R intervals), RR50 (Number of the RR interval differing from the preceding RR interval by more than 50 msec), and the like are known. CVRR is a numerical value obtained by dividing the standard deviation of R-R intervals in a predetermined period or a predetermined number of R-R intervals by the average value and multiplying the result by 100. The CVRR is effective to know the degree of variation of R-R intervals in a certain period.

RR50 is an index of the parasympathetic function proposed by Ewings et al. in England. The RR50 indicates the ratio of R-R intervals for which the interval to an adjacent R-R interval is 50 msec or more to R-R intervals in a predetermined period or a predetermined number of R-R intervals. If a person is mentally relaxed, the R-R interval changes largely in a short time, and therefore, the count of RR50 is considered to be large. In this way, the degree of mental relaxation or the degree of tension can be estimated based on the RR50.

A method of analyzing the frequency component of a fluctuation of R-R intervals is often used as well. The power spectrum of the fluctuation frequency of the R-R interval is obtained by fast Fourier transform (FFT) and represented by the ratio (LF/HF) of power (LF: low frequency component) of about 0.1 Hz to power (HF: high frequency component) of about 0.25 Hz. In LF/HF analysis, a large value is considered to indicate an increase in the parasympathetic function. It is estimated that a person is mentally tense as the value increases.

Figure 7:
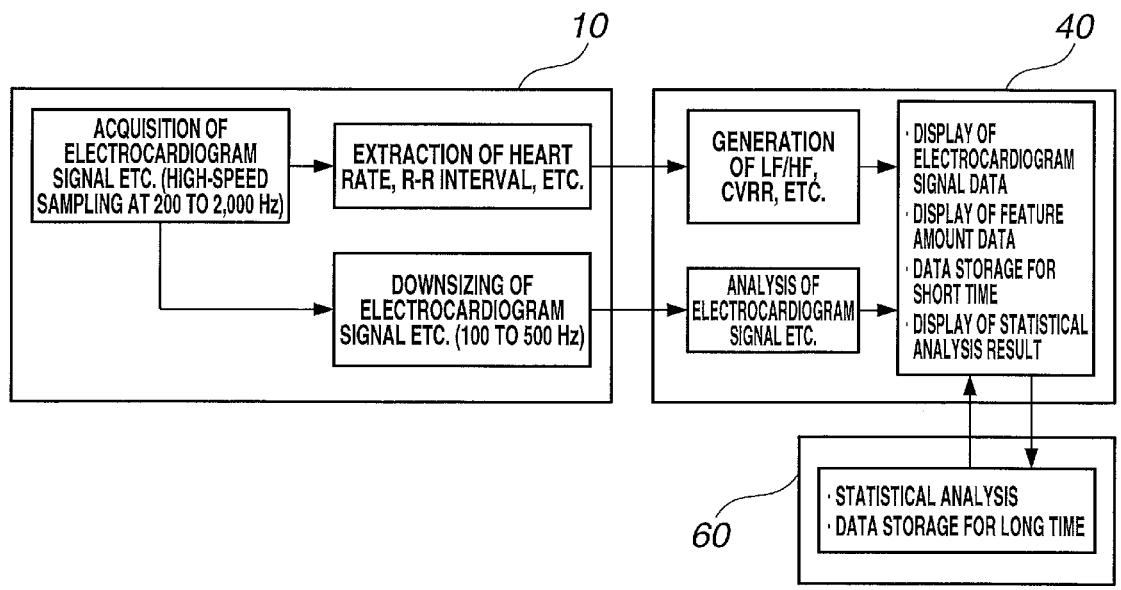
FIG. 7 is a block diagram for explaining processing division in the biological signal measurement system according to the first embodiment of the present invention.

In a biological signal measurement system shown in FIG. 7, extraction of the feature amount data (first feature amount data) of the electrocardiogram signal such as the R-R interval is executed by the biological signal measurement apparatus 10 because it is processing of light operation load using a simple operation algorithm. Generation of additional feature amount data (second feature amount data) by statistical analysis of the feature amount such as CVRR or LF/HF of heavy operation load is executed by the portable terminal 40 having a high operation capability.

The biological signal measurement apparatus 10 transmits, to the portable terminal 40, data (corresponding to a data size corresponding to a sampling rate of, for example, 100 to 500 Hz) downsized from electrocardiogram signal data obtained by sampling at a high sampling rate (for example, 200 to 2,000 Hz), thereby suppressing the transmitted data amount. In the cloud server 60, statistical analysis for a plurality of users is executed using analysis results transmitted from a plurality of portable terminals.

For example, if an electrocardiogram signal is sampled at 1 kHz, and a data amount per sample is 2 bytes, the data amount for 24 hrs is 172.8 MB. To transfer such rich data to the portable terminal or the cloud server, a long time and much power are inefficiently needed. On the other hand, the heart rate is 200 beats/min at most. Hence, the data amount is only 576 kB in 24 hrs even if the R-R interval is expressed by 2 bytes. In this way, more types of biological information can be handled while reducing the communication load.

To implement a long-time operation with low power consumption, the communication capacity between the biological signal measurement apparatus 10 and the portable terminal 40 is made as small as possible as compared to the communication capacity of the wireless LAN (for example, WiFi) method or cellular method between the portable terminal 40 and the public network 50. For example, use of the Bluetooth (Bluetooth 2.1) or Bluetooth low energy (Bluetooth 4.0) standard can be considered. The communication capacity of Bluetooth 2.1 is about 1.3 Mbps, and that of Bluetooth 4.0 is 1 Mbps, which are orders of magnitude smaller than 10 Mbps to 54 Mbps in the general WiFi 802.11 standard or 100 Mbps at maximum downlink in LTE.

It is self-evident that transferring a large amount of data via a communication means of a small communication capacity leads to an increase in the communication time. Hence, in this embodiment, processing is divided to cause the biological signal measurement apparatus 10, the portable terminal 40 such as a smartphone, and the cloud server 60 to share data analysis and accumulation, and the data transfer amount is optimized in accordance with the communication capacity between the apparatuses, thereby enabling an efficient data flow suitable for the communication capability of each apparatus and the communication means between the apparatuses.

Figure 8:
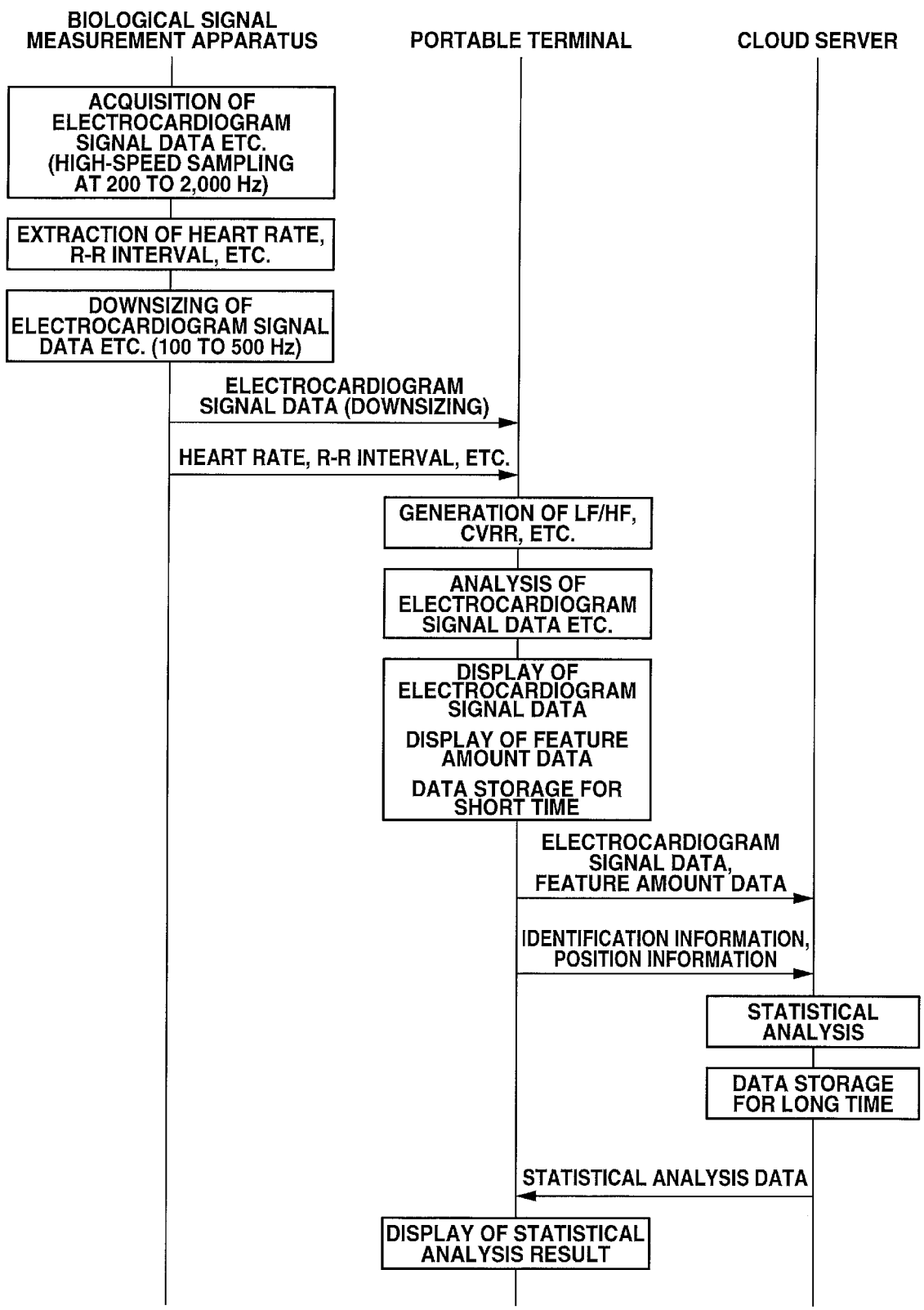
FIG. 8 is a sequence chart for explaining processing division in the biological signal measurement system according to the first embodiment of the present invention and the procedure of processing performed by each apparatus.

In FIG. 8, when acquiring electrocardiogram signal data, sampling at a high sampling rate of 200 to 2,000 Hz is executed aiming at acquiring accurate electrocardiogram signal data of medical level. In addition, the biological signal measurement apparatus extracts feature amount data such as the heart rate, the R-R interval, and the like based on the accurate electrocardiogram signal data.

If Bluetooth 2.1 or Bluetooth 4.0 described above is selected as the wireless communication method between the biological signal measurement apparatus and the portable terminal, the wireless communication speed is limited to about 1 Mbps. For this reason, the electrocardiogram signal data acquired by the biological signal measurement apparatus is not directly transmitted to the portable terminal but downsized, that is, thinned to a data size corresponding to a sampling rate of, for example, 100 to 500 Hz and then transmitted to the portable terminal. At the same time, feature amount data such as the R-R interval extracted from the accurate electrocardiogram signal data, whose data size is much smaller than that of the electrocardiogram signal data, is also transmitted to the portable terminal. The data contents to be transmitted and the data transfer amount are thus optimized in accordance with the communication capacity to the portable terminal, and the data transmission time is shortened, thereby reducing power consumption.

The portable terminal has a faster processor and a larger memory as compared to the biological signal measurement apparatus, and can perform analysis of heavier processing load. Hence, using the transmitted electrocardiogram signal data or feature amount data such as the R-R interval data, the portable terminal displays the data or generates another feature amount data by statistical analysis of the feature amount data and the like. As the analysis to be performed in the portable terminal, ST analysis (the variation in the interval between an S wave and a T wave) in the electrocardiogram waveform, detection of the presence/absence of an allorhythmic pulse, and breath analysis can be considered in addition to the above-described LF/HF analysis and stress analysis based on the variation in the R-R interval.

Next, the portable terminal uploads any one of the received electrocardiogram signal data and feature amount data to the cloud server as needed. Not all data need always be transmitted, and data to be stored or undergo statistical analysis in the server may selectively be transmitted as needed. The portable terminal can also upload the identification information of the living body, the position information of the portable terminal, and the like in addition to the electrocardiogram signal data or the feature amount data. The cloud server can perform statistical analysis using these pieces of information transmitted from a plurality of portable terminals. The cloud server can feed back the statistical analysis data to the portable terminal, and can also present it to use by a third party such as a hospital.

When the biological information such as the electrocardiogram signal data and feature amount data is uploaded to the cloud server as needed, a shortage in the memory capacity of the portable terminal can be avoided to prevent a data loss. When the portable terminal is disconnected from the network, the feature amount and waveform are held in the memory of the portable terminal. When connection with the network is reestablished, the data are uploaded to the cloud server.

Figure 9:
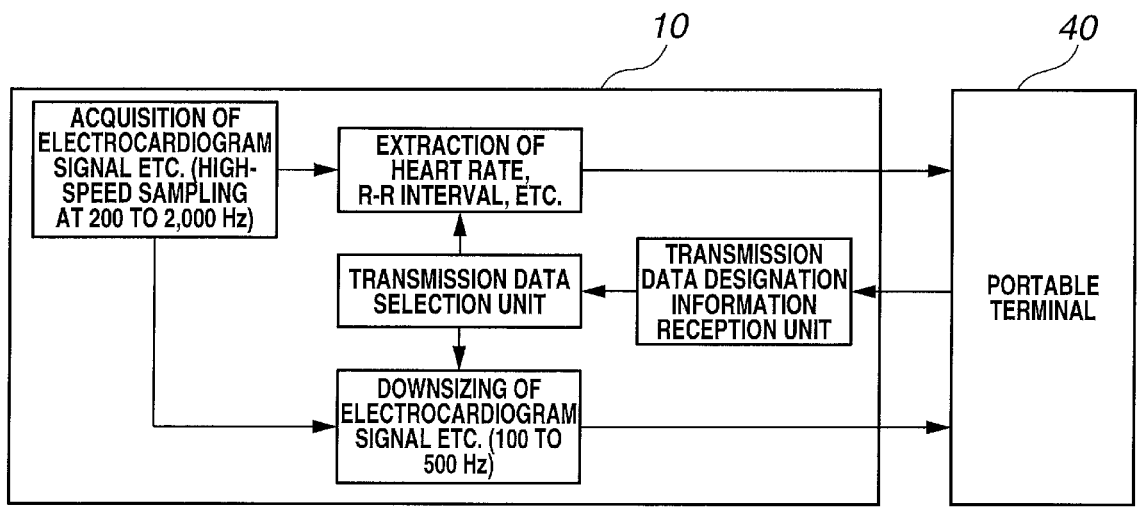
FIG. 9 is a block diagram for explaining processing division in the biological signal measurement system in a case in which the biological signal measurement apparatus includes a transmission data selection unit.

The biological signal measurement apparatus 10 may be able to select data to be transmitted based on an instruction from the portable terminal 40. Referring to FIG. 9, the biological signal measurement apparatus 10 includes a transmission data selection unit and a transmission data designation information reception unit. Determination to select data to be transmitted is done by the portable terminal 40. The biological signal measurement apparatus 10 selects at least one of second biological digital data and first feature amount data based on transmission data designation information transmitted from the portable terminal 40, and transmits the data to the portable terminal.

As the criterion for transmission data selection by the portable terminal 40, for example, a communication environment such as a packet loss ratio between the biological signal measurement apparatus 10 and the portable terminal 40 can be considered. If the communication environment between the biological signal measurement apparatus 10 and the portable terminal 40 deteriorates, transmission of biological digital data can be disabled to further decrease the data communication amount. Additionally, based on the biological digital data or feature amount data analysis result transmitted from the biological signal measurement apparatus 10, the reliability of feature amount data, the condition of the user, or the like may be estimated, and data that needs to be transmitted may be selected.

As described above, according to this embodiment, it is possible to provide a biological signal measurement system that optimizes processing division and the data transfer amount between the apparatuses that constitute the system of measuring biological information, thereby simultaneously implementing acquisition of an accurate biological signal of medical level and reduction of the size and power consumption of the biological signal measurement apparatus and browsing and analyzing a biological signal in real time.

Second Embodiment

A biological information measurement apparatus according to the second embodiment will be described below.

Figure 10:
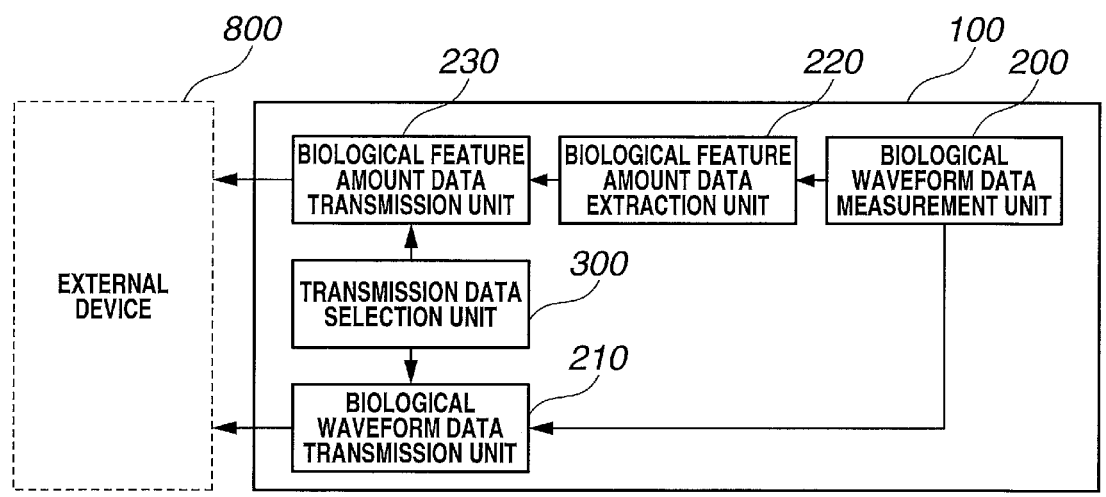
FIG. 10 is a functional block diagram of a biological information measurement apparatus according to the second embodiment of the present invention.

A biological information measurement apparatus 100 shown in FIG. 10 includes a biological waveform data measurement unit 200 configured to measure biological waveform data, a biological waveform data transmission unit 210 configured to transmit the biological waveform data to an external device 800, a biological feature amount data extraction unit 220 configured to extract biological feature amount data from the biological waveform data, a biological feature amount data transmission unit 230 configured to transmit the biological feature amount data to the external device 800, and a transmission data selection unit 300 configured to select data to be transmitted to the external device 800.

Note that the biological information measurement apparatus 100 is preferably a watch type, ring type, glasses type, wear-integrated type, paste type, or the like such that the user can wear it and monitor the physical/mental condition in daily life for a long time.

The biological waveform data measurement unit 200 in a case in which the biological waveform data is an electrocardiogram waveform will be described first. The electrocardiogram waveform is obtained by bringing electrodes into contact with the body surface and observing the electrical activity of the heart. As the electrocardiogram waveform leading method, that is, the electrode arrangement, there are various types using limbs and chest.

For example, in the CC5 lead used when monitoring the electrocardiogram waveform for a long time, the electrodes are arranged on the left and right chests. Note that when measuring the electrocardiogram waveform, since the voltage of the electrocardiogram waveform is generally several mV or less, a detected voltage may be amplified to a predetermined signal level using an analog circuit or the like, and unnecessary noise and fluctuation may be filtered. When this voltage is sampled using an analog-to-digital converter, a digitized electrocardiogram waveform can be obtained. An electrocardiogram waveform having a sufficient accuracy can be obtained by performing sampling at, for example, 1 kHz and 12 bits.

Note that after the digital signal conversion, unnecessary noise and fluctuation may further be removed by digital filtering.

Figure 11:
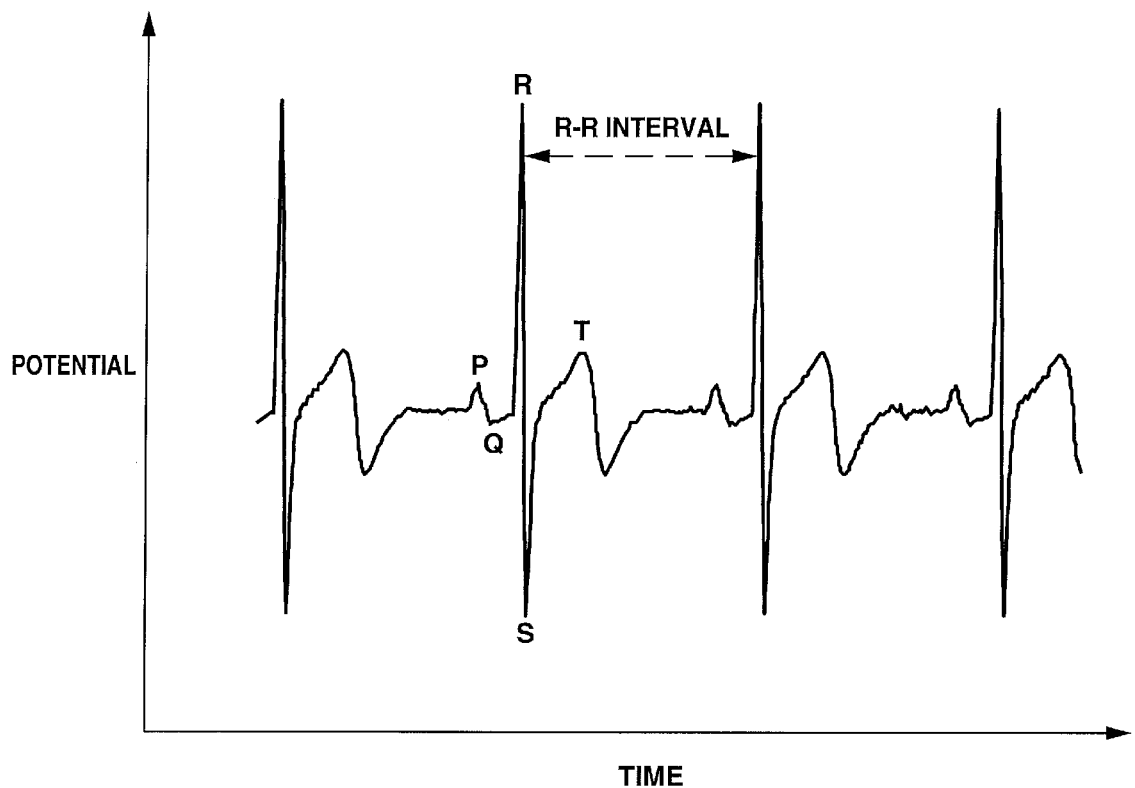
FIG. 11 is a graph showing an example of measurement of an electrocardiogram waveform that is an example of biological waveform data.

The biological feature amount data extraction unit 220 in a case in which the biological waveform data is an electrocardiogram waveform will be described next. In the electrocardiogram waveform measurement example of FIG. 11, the electrocardiogram waveform is formed from components such as a P-QRS-T wave reflecting the activity of an atrium or a ventricle. The time interval between adjacent R waves is biological feature amount data called an R-R interval. When the reciprocals of the R-R intervals are averaged, a heart rate is obtained. To detect an R wave from the electrocardiogram waveform, a method of detecting the peak of the amplitude of the electrocardiogram waveform or a method of detecting the peak of the derivative of the electrocardiogram waveform is used. For example, Japanese Patent Laid-Open No. 2003-561 discloses an arrangement that recognizes an R wave by a threshold based on the amplitude between the crest and the trough of a waveform.

The biological information measurement apparatus 100 transmits the biological waveform data and/or the biological feature amount data acquired in this above-described way to the external device 800. The external device 800 is, for example, a smartphone, an information terminal of a watch type, or a personal computer. As the biological waveform data transmission unit 210 and the biological feature amount data transmission unit 230, for example, a short-range wireless technology such as Bluetooth®, Zigbee®, or Wi-Fi can be used.

Since the transmission data selection unit 300 is provided, the biological information measurement apparatus 100 can select whether to transmit biological waveform data to the external device 800, whether to transmit biological feature amount data, or whether to transmit both of them. This enables an operation of usually transmitting biological feature amount data with a small data amount to reduce power consumption and only when necessary, transmitting biological waveform data including abundant information.

If the sampling frequency is 1 kHz, and the resolution is 12 bits, the data amount of biological waveform data, for example, an electrocardiogram waveform is 12 kbps. On the other hand, R-R interval data that is biological feature amount data can be expressed by 12 bits per data if the time resolution is 1 msec, and the range is 0 to 4,095 msec. If the average heart rate is 100 bpm, the average data amount is 20 bps.

Hence, if the electrocardiogram waveform is unnecessary, only the R-R interval is transmitted, thereby largely decreasing the data amount. This makes it possible to decrease the communication amount, reduce the power consumption of the biological information measurement apparatus 100 or the external device 800, and continuously measure biological information for a long time.

Note that the biological information measurement apparatus 100 may intermittently transmit measured data to the external device 800 while temporarily accumulating the measured data. When transmitting the above-described electrocardiogram waveform data, if, for example, 10 data are assumed to be transmitted at once, the electrocardiogram waveform data is transmitted at an interval of 10 msec.

Additionally, as for the R-R interval data, if 10 data are assumed to be transmitted at once, an R-R interval of 200 msec at the minimum can be handled by transmitting the data at an interval of 2 sec. When the data transmission interval is optimized in accordance with the data to be transmitted in the above-described way, data transmission of high power efficiency can be implemented.

As described above, according to this embodiment, it is possible to select whether to transmit one or both of biological waveform data and biological feature amount data. Hence, if biological waveform data is unnecessary, only biological feature amount data is transmitted, thereby suppressing the communication amount and implementing downsizing and long life of a battery.

If necessary, biological waveform data is transmitted, and a biological feature amount is extracted by the external device having a high information processing capability. This makes it possible to reduce an extraction failure or an extraction error of a biological feature amount data.

Third Embodiment

A biological information measurement apparatus according to the third embodiment will be described below.

Figure 12:
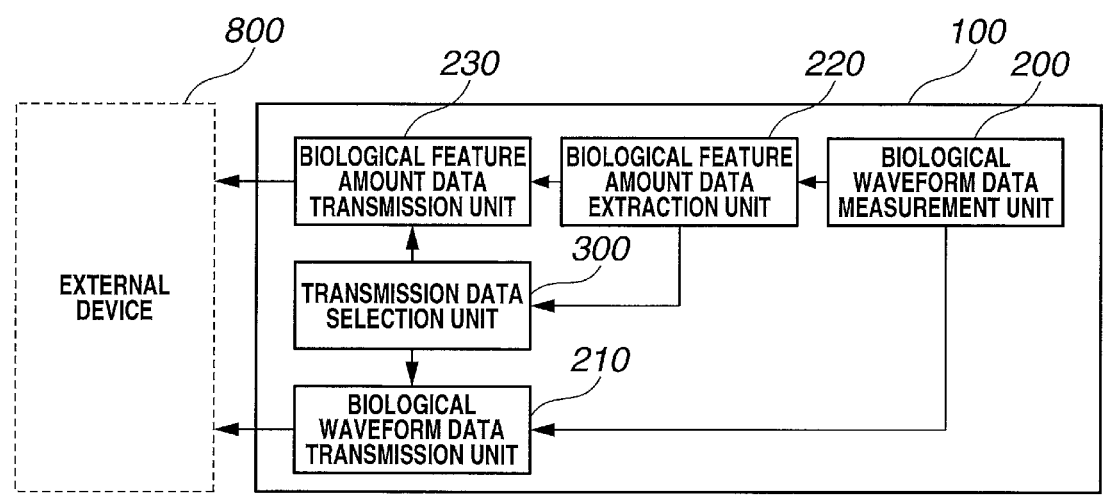
FIG. 12 is a functional block diagram of a biological information measurement apparatus according to the third embodiment of the present invention.
Figure 13:
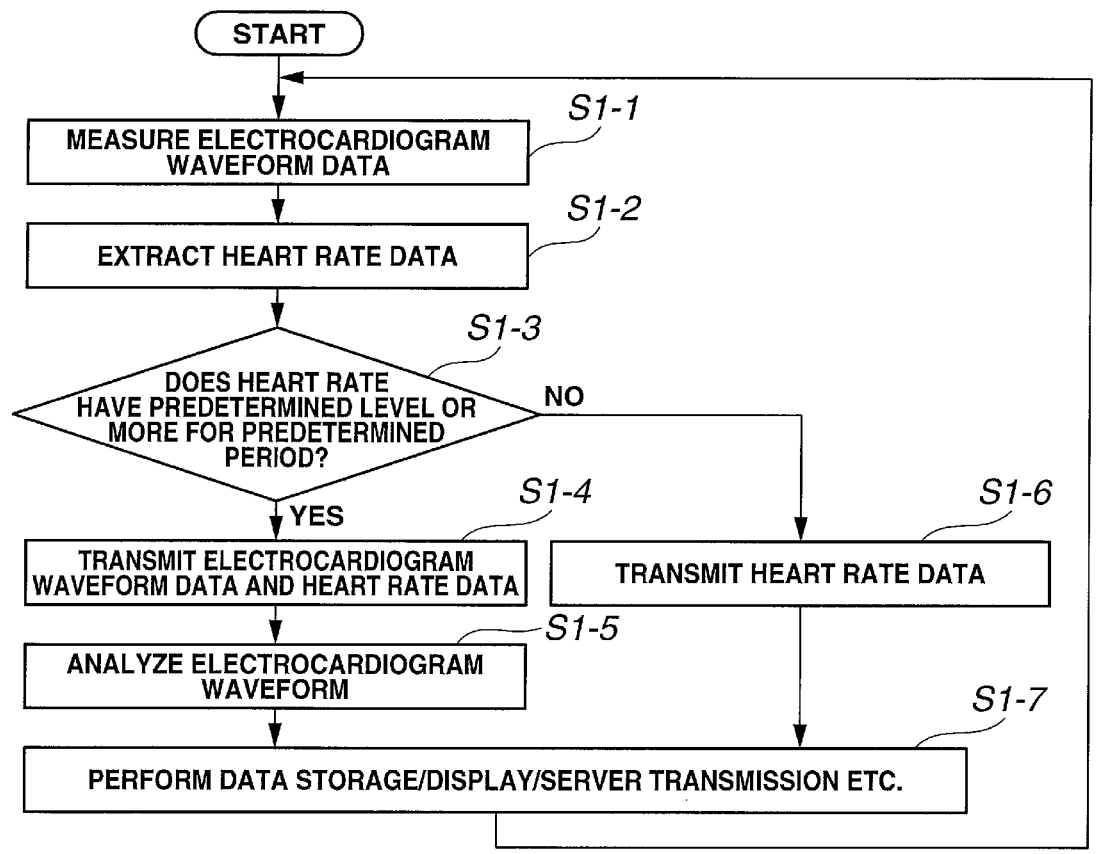
FIG. 13 is a flowchart for explaining the procedure of biological information measurement according to the third embodiment of the present invention.

In FIGS. 12 and 13, transmission data is selected based on extracted biological feature amount data. In this embodiment, a case in which biological waveform data is an electrocardiogram waveform, and biological feature amount data is a heart rate will be explained.

First, a biological information measurement apparatus 100 measures electrocardiogram waveform data by a biological waveform data measurement unit 200 (step S1-1) and extracts heart rate data from the electrocardiogram waveform data by a biological feature amount data extraction unit 220 (step S1-2). A transmission data selection unit 300 selects data to be transmitted based on the extracted biological feature amount data (step S1-3).

If the heart rate has a predetermined level or more for a predetermined period, the condition of the user may have a problem. In this case, the heart rate data and the electrocardiogram waveform data are transmitted to an external device 800 by a biological feature amount data transmission unit 230 and a biological waveform data transmission unit 210, respectively (step S1-4). The electrocardiogram waveform is analyzed in the external device 800 to analyze whether a health problem has occurred or not (step S1-5).

On the other hand, if the heart rate does not have the predetermined level or more for the predetermined period, only the heart rate data is transmitted by the biological feature amount data transmission unit 230, thereby reducing power consumption (step S1-6). The external device 800 receives the data from the biological information measurement apparatus 100, and performs an operation of analyzing, storing, or displaying the data or transmitting the data to a server as needed (step S1-7).

In this embodiment, the heart rate is used as the criterion for transmission data selection. However, the present invention is not limited to this. For example, if the variation in the R-R interval has a predetermined level or less for a predetermined period, it may be determined that the user is in a strong tension state, and the electrocardiogram waveform may be transmitted. In addition, since the electrocardiogram waveform includes a component derived from a breath, a feature amount associated with the breath may be extracted from the electrocardiogram waveform, and the electrocardiogram waveform may be transmitted when the breach frequency falls to a predetermined level or less.

As described above, in this embodiment, the biological information measurement apparatus selects data to be transmitted based on extracted biological feature amount data, transmits a biological waveform data signal with an abundant information amount only when necessary in accordance with the condition of the user, and transmits biological feature amount data otherwise, thereby enabling an efficient operation while reducing power consumption.

Since the data to be transmitted is selected based on the biological feature amount data extraction result, the biological information measurement apparatus can automatically select the data to be transmitted.

Fourth Embodiment

A biological information measurement apparatus according to the fourth embodiment will be described below.

Figure 14:
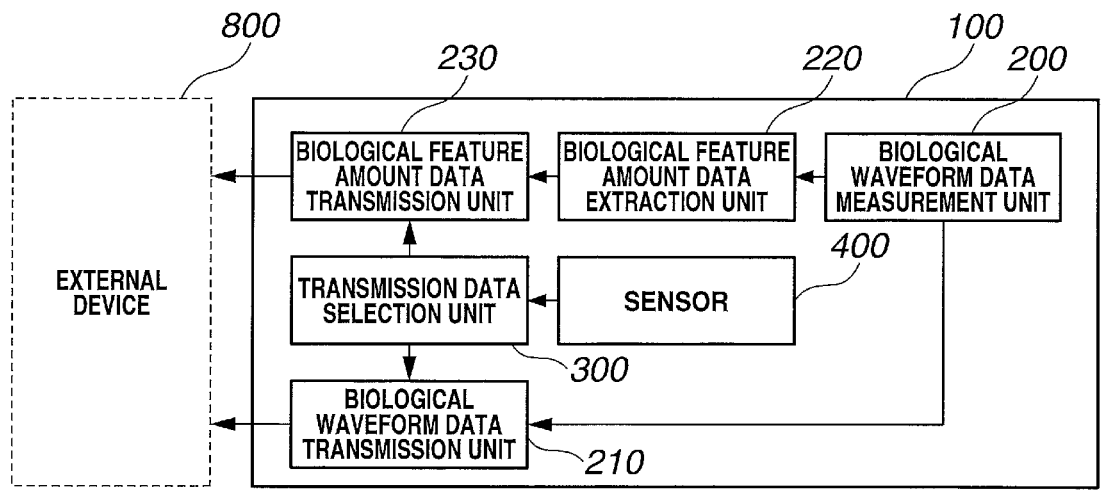
FIG. 14 is a functional block diagram of a biological information measurement apparatus according to the fourth embodiment of the present invention.

In FIG. 14, a biological information measurement apparatus 100 further includes a sensor 400, and selects transmission data based on the state of the sensor 400. As the sensor 400, for example, a push button switch, a body temperature sensor, an outdoor temperature sensor, or a battery voltage sensor is usable.

Figure 15:
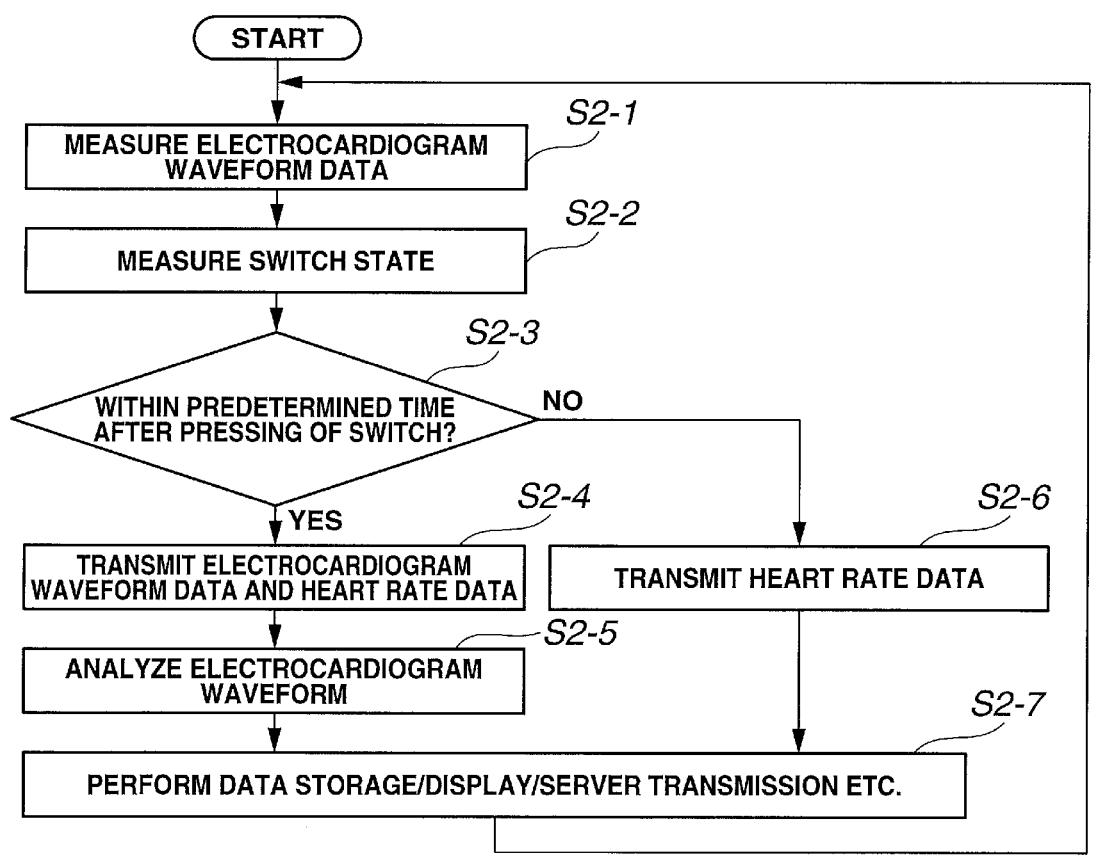
FIG. 15 is a flowchart for explaining the procedure of biological information measurement according to the fourth embodiment of the present invention.

A case in which biological waveform data is an electrocardiogram waveform, a biological feature amount is a heart rate, and the sensor 400 is a push button switch will be explained with reference to FIG. 15.

In this embodiment, after electrocardiogram waveform data is measured (step S2-1), and the state of the push button switch is measured (step S2-2). If a predetermined time has elapsed after the pressing of the push button switch, only the heart rate is transmitted, thereby reducing power consumption (step S2-6). If the user feels a disorder such as a pain in the heart or difficulty in breathing, the push button switch is pressed. Only when the predetermined time or less has elapsed after the pressing of the push button switch, the electrocardiogram waveform data and the heart rate are transmitted (step S2-4). The electrocardiogram waveform is analyzed in an external device 800 to analyze whether a health problem has occurred or not (step S2-5). By providing the push button switch that receives a user input, the data to be transmitted can be selected in accordance with the user's intention.

In a case in which the sensor 400 is a body temperature sensor or an outdoor temperature sensor, if the body temperature or outdoor temperature is a predetermined value or more, electrocardiogram waveform data and heart rate data are transmitted. Otherwise, only heart rate data is transmitted.

In a case in which the sensor 400 is a battery voltage sensor, if the battery level of the biological information measurement apparatus 100 is sufficient, electrocardiogram waveform data and heart rate data are transmitted. Otherwise, only heart rate data is transmitted, thereby making the battery life long.

Figure 16:
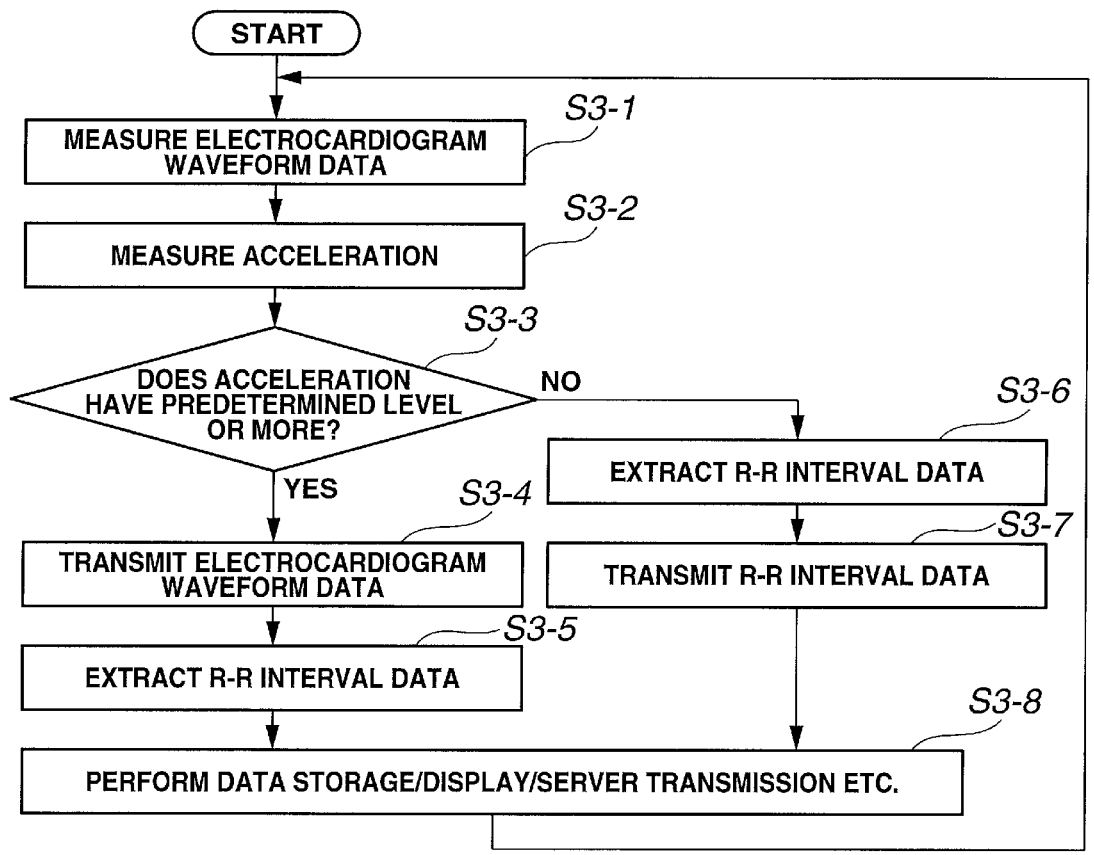
FIG. 16 is a flowchart for explaining the procedure of biological information measurement in a case in which data to be transmitted is selected based on an acceleration sensor.

A case in which the biological information measurement apparatus 100 further includes the sensor 400, and selects transmission data based on the state of the sensor 400 has been described with reference to FIG. 14. A reliability determination unit configured to determine the reliability of feature amount data may be provided in place of the sensor, and transmission data may be selected based on the determination result. In FIG. 16, the biological waveform data is an electrocardiogram waveform, the biological feature amount is an R-R interval, and the reliability determination unit is an acceleration sensor.

The biological information measurement apparatus 100 measures electrocardiogram waveform data (step S3-1) and further measures the body acceleration using the acceleration sensor (step S3-2). If the acceleration is a predetermined level or more, the user may be making an active motion. In this case, the contact of an electrode pasted to the skin to measure the electrocardiogram waveform may be unstable, or an electromyogram signal may be mixed to cause a disturbance in the electrocardiogram waveform. If the electrocardiogram waveform is disturbed, the R-R interval data extraction algorithm included in a biological feature amount data extraction unit 220 of the biological information measurement apparatus 100 cannot function well, and an R wave may erroneously be detected.

Upon determining that the acceleration is a predetermined level or more, and the reliability of the R-R interval extraction is low, the biological information measurement apparatus 100 transmits not the R-R interval data but only the electrocardiogram waveform data to an external device 800 (step S3-4). The external device 800 having a higher information processing capability extracts the R-R interval using an advanced algorithm. More specifically, a method of calculating the autocorrelation of an electrocardiogram waveform and identifying the periodicity of the electrocardiogram waveform, a method of storing the information of an electrocardiogram waveform on rest in advance and comparing the information with a measured electrocardiogram waveform to remove the influence of an external disturbance, or the like can be considered.

On the other hand, if the acceleration is lower than the predetermined level, it can be determined that the reliability of biological feature amount extraction is not low. Hence, the biological feature amount data extraction unit 220 of the biological information measurement apparatus 100 extracts the R-R interval data (step S3-6), and only the R-R interval data is transmitted to the external device 800 (step S3-7), thereby reducing power consumption.

The biological waveform data transmission unit that determines the reliability of biological feature amount data is not limited to the acceleration sensor. For example, in a case in which an impedance sensor configured to measure the impedance between the skin and an electrode used to measure the electrocardiogram waveform is provided, if the impedance between the electrode and the skin is high, or the variation in the impedance is large, it is determined that the reliability of biological feature amount data is low, and the electrocardiogram waveform data is transmitted to the external device. In a case in which a pressure sensor configured to measure the pressure between the skin and an electrode is used, if the contact pressure between the electrode and the skin is low, or the variation in the contact pressure is large, it is determined that the reliability of biological feature amount data is low, and the electrocardiogram waveform data is transmitted to the external device.

As described above, in this embodiment, data to be transmitted is selected based on the state of the sensor provided in the biological information measurement apparatus. It is therefore possible to determine, in accordance with a user designation or the situation of the user, whether biological waveform data needs to be transmitted.

Fifth Embodiment

A biological information measurement apparatus according to the fifth embodiment will be described below.

Figure 17:
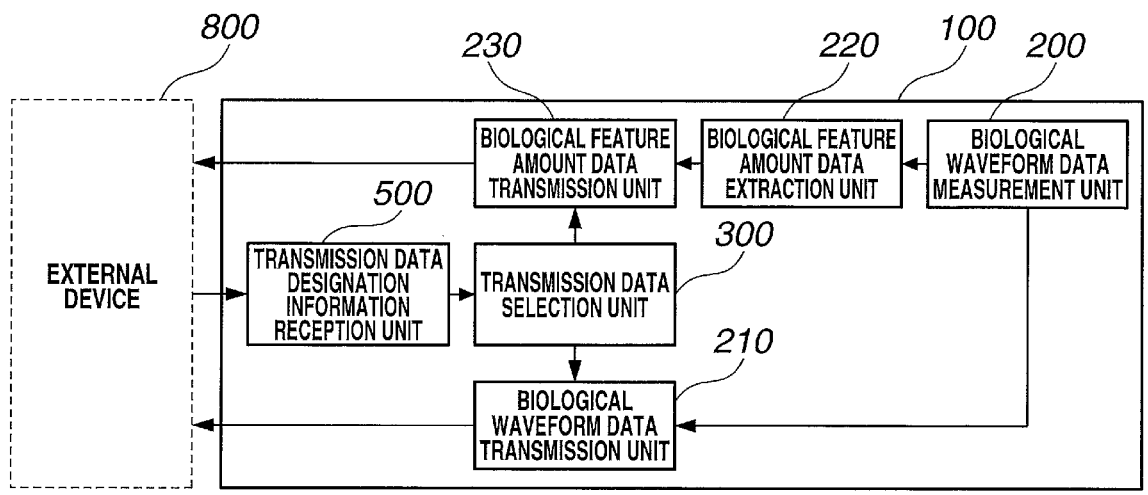
FIG. 17 is a functional block diagram of a biological information measurement apparatus according to the fifth embodiment of the present invention.

In FIG. 17, a biological information measurement apparatus 100 includes a transmission data designation information reception unit 500. In this embodiment, an external device 800 determines selection of data to be transmitted by the biological information measurement apparatus 100. A transmission data selection unit 300 receives transmission data designation information from the external device 800, and selects data to be transmitted based on the received transmission data designation information.

Figure 18:
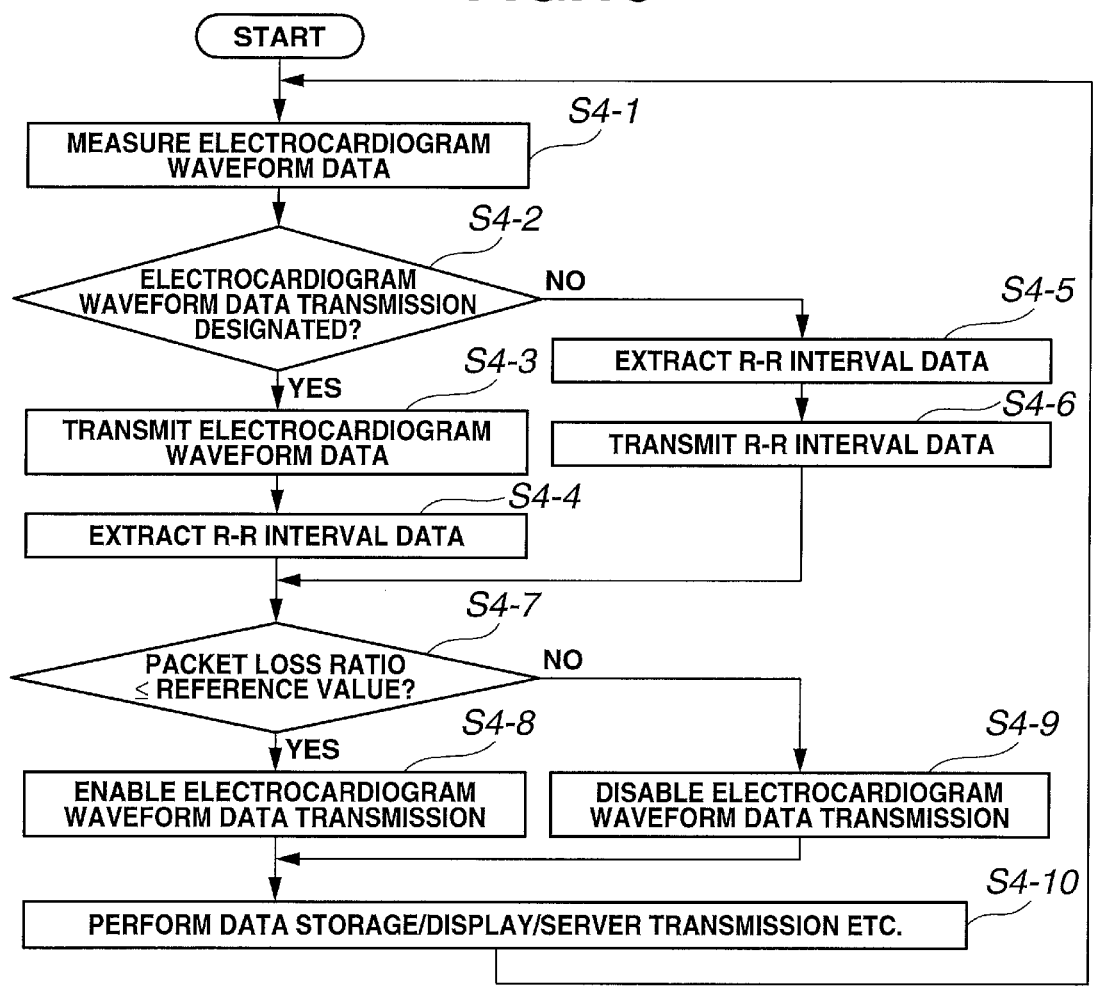
FIG. 18 is a flowchart for explaining the procedure of biological information measurement according to the fifth embodiment of the present invention.

In FIG. 18, biological waveform data is an electrocardiogram waveform, a biological feature amount is an R-R interval, and the external device 800 determines data to be transmitted based on the communication environment.

First, the biological information measurement apparatus 100 measures electrocardiogram waveform data (step S4-1). Next, the biological information measurement apparatus 100 confirms whether transmission of electrocardiogram waveform data is designated by the external device 800 (step S4-2). If the transmission of electrocardiogram waveform data is designated, the electrocardiogram waveform data is transmitted to the external device 800 (step S4-3). The external device 800 extracts R-R interval data from the received electrocardiogram waveform data (step S4-4).

On the other hand, if the transmission of electrocardiogram waveform data is not designated, a biological feature amount data extraction unit 220 of the biological information measurement apparatus 100 extracts R-R interval data from the electrocardiogram waveform data (step S4-5), and transmits it to the external device 800 (step S4-6). The external device 800 performs data transmission/reception and measures the packet loss ratio of the communication with the biological information measurement apparatus 100 (step S4-7).

The packet loss ratio can be measured by, for example, adding a serial number to each packet transmitted/received by the biological information measurement apparatus 100 and the external device 800 and checking whether a missing serial number exists. If the packet loss ratio is equal to or less than a reference value, it can be determined that the communication environment is good, and a data loss hardly occurs. Hence, the electrocardiogram waveform data with a large information amount is transmitted (step S4-8).

On the other hand, if the packet loss ratio is more than the reference value, the communication environment is not good. Even if the electrocardiogram waveform data with a large information amount is transmitted, the data is partially lost at a high possibility. Hence, the transmission of electrocardiogram waveform data is disabled, and R-R interval data with a small information amount and little risk is transmitted (step S4-9). Whether the communication environment is good or not may be determined by detecting not only the packet loss ratio but also the ambient radio condition by the external device 800.

As for the criterion used by the external device 800 for transmission data selection, based on not only the communication environment but also biological waveform data or biological feature amount data analysis result transmitted from the biological information measurement apparatus 100, the condition of the user or the like may be estimated, and it may be determined whether biological waveform data is necessary.

Figure 19:
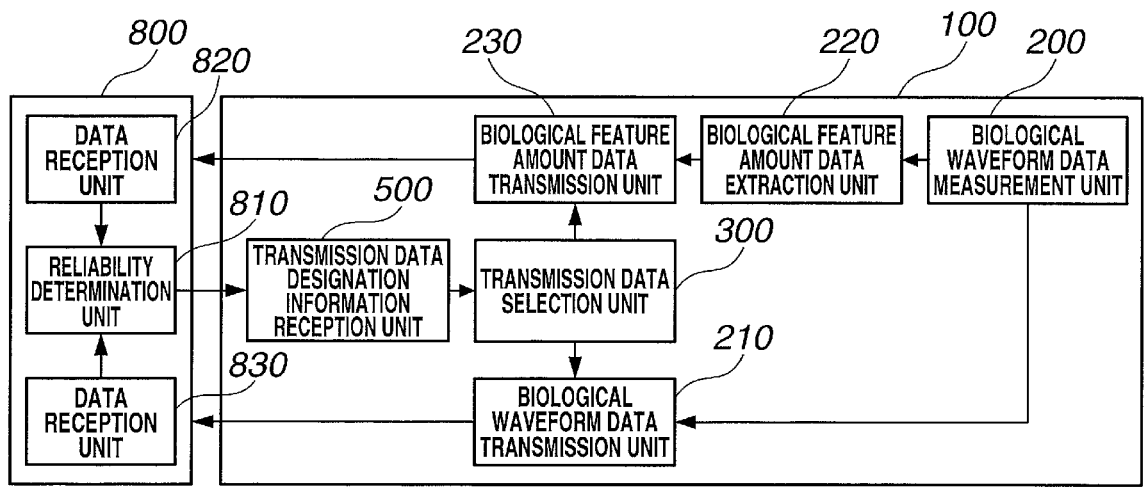
FIG. 19 is a block diagram of a biological signal measurement system that selects data to be transmitted based on the reliability of feature amount data.

For example, the external device 800 may determine selection of data to be transmitted based on the reliability of biological feature amount data. In FIG. 19, the external device 800 includes a data reception unit 830 configured to receive biological waveform data from the biological information measurement apparatus 100, a data reception unit 820 configured to receive biological feature amount data, and a reliability determination unit 810 configured to determine the reliability of the biological feature amount data.

The external device 800 determines the selection of data to be transmitted by the biological information measurement apparatus 100 based on the reliability of biological feature amount data, and transmits transmission data designation information to the biological information measurement apparatus 100. The transmission data selection unit 300 of the biological information measurement apparatus 100 selects data to be transmitted based on the transmission data designation information received from the external device 800.

In FIG. 20, biological waveform data is an electrocardiogram waveform, a biological feature amount is an R-R interval, and the external device 800 designates data to be transmitted based on the reliability of feature amount data.

First, the biological information measurement apparatus 100 measures electrocardiogram waveform data (step S5-1). Next, the biological information measurement apparatus 100 confirms whether transmission of electrocardiogram waveform data is designated by the external device 800 (step S5-2). If the transmission of electrocardiogram waveform data is designated, the electrocardiogram waveform data is transmitted to the external device 800 (step S5-3). The external device 800 extracts R-R interval data from the received electrocardiogram waveform data (step S5-4).

On the other hand, if the transmission of electrocardiogram waveform data is not designated, the biological feature amount data extraction unit 220 of the biological information measurement apparatus 100 extracts R-R interval data from the electrocardiogram waveform data (step S5-5), and transmits it to the external device 800 (step S5-6). The external device 800 determines whether the reliability of the extracted or received R-R interval data is equal to or less than a reference value (step S5-7).

As for the method of determining the reliability of R-R interval data, for example, the absolute value of the difference between the extracted or received R-R interval data and existing R-R interval data is calculated. If the absolute value of the difference is equal to or larger than a predetermined threshold, the reliability can be determined to be low. For example, the R-R interval hardly abruptly varies in a normal state. However, if large noise is mixed, and a detection error occurs, the R-R interval abruptly varies, and it can be estimated that the reliability is low at a high possibility. By analyzing feature amount data this way, the reliability of the data can be evaluated.

If the reliability of the R-R interval data is evaluated in this way, and it is determined that the reliability is low, the external device 800 enables transmission of electrocardiogram waveform data to the biological information measurement apparatus 100 (step S5-8).

On the other hand, upon determining that the reliability is high, the external device 800 disables transmission of electrocardiogram waveform data to the biological information measurement apparatus 100 (step S5-9).

As described above, in this embodiment, the biological information measurement apparatus includes the transmission data designation information reception unit, and selects data to be transmitted based on received transmission data designation information.

This allows the advanced external device to appropriately select data to be transmitted by the biological information measurement apparatus.

Sixth Embodiment

A biological information measurement apparatus according to the sixth embodiment will be described below.

In FIG. 21, a biological information measurement apparatus 100 includes an algorithm change information reception unit 600 and an extraction algorithm changing unit 700.

Figure 22:
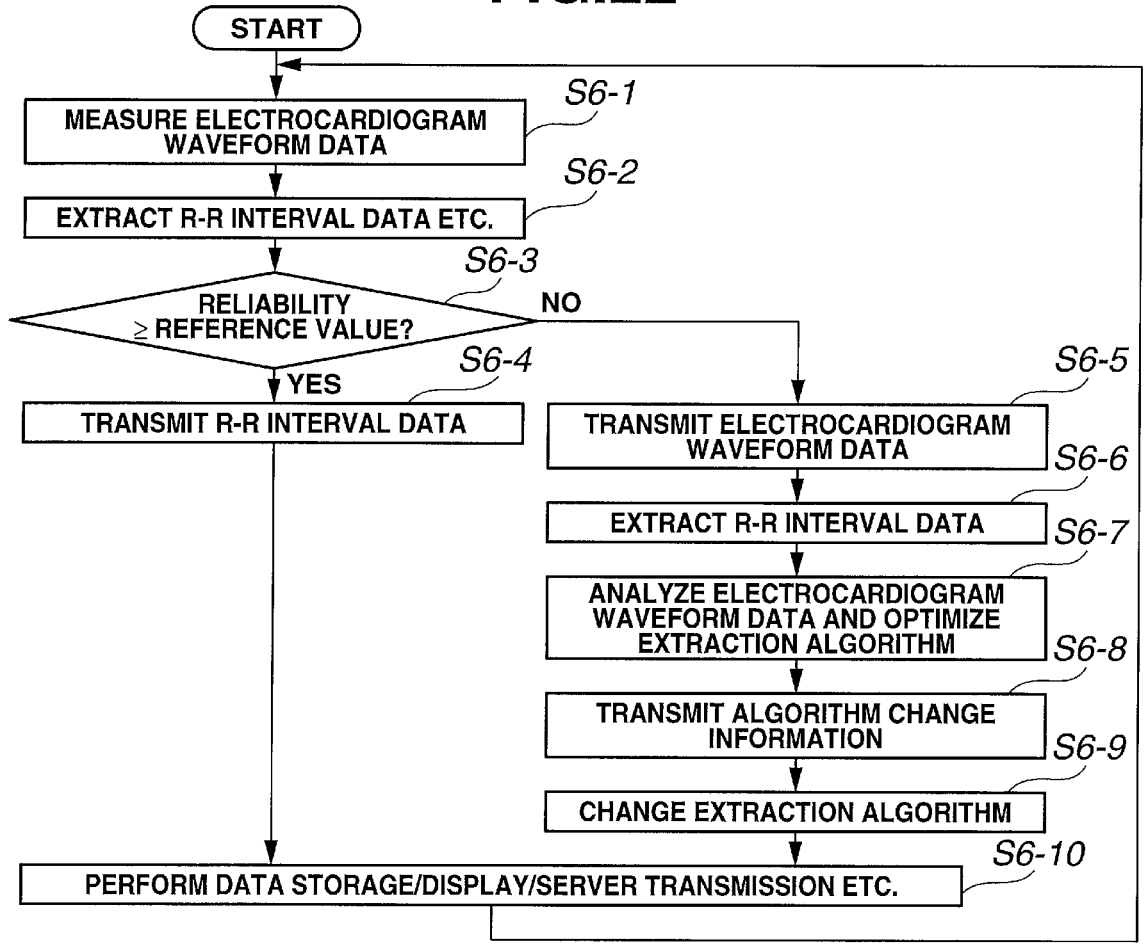
FIG. 22 is a flowchart for explaining a procedure of changing a biological feature amount extraction algorithm according to the sixth embodiment of the present invention.
Figure 23A:
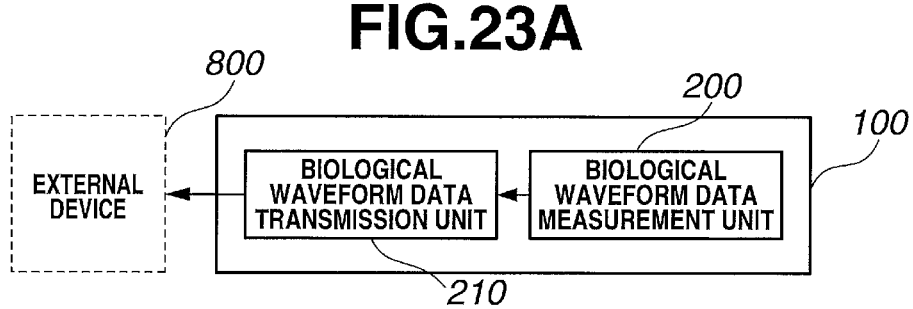
FIG. 23A is an example of a functional block diagram of a conventional biological information measurement apparatus.
Figure 23B:
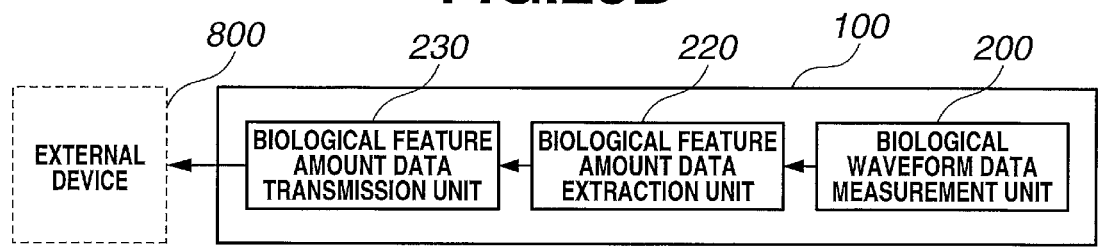
FIG. 23B is another example of the functional block diagram of the conventional biological information measurement apparatus.

In FIG. 22, biological waveform data is an electrocardiogram waveform, a biological feature amount is an R-R interval, and an external device 800 changes an R-R interval data extraction algorithm.

First, the biological information measurement apparatus 100 measures an electrocardiogram waveform (step S6-1), extracts R-R interval data (step S6-2), and evaluates the reliability of the extracted R-R interval data (step S6-3). For example, the absolute value of the difference between the extracted R-R interval data and R-R interval data extracted previously is calculated. If the absolute value of the difference is smaller than a predetermined threshold, the reliability is determined to be high. This is a method of evaluating reliability using the fact that the R-R interval data of a human hardly abruptly varies in a normal state. The threshold used to evaluate the reliability is set to, for example, 100 msec.

If the reliability of the R-R interval data is evaluated in this way, and it is determined that the reliability is high, the biological information measurement apparatus transmits the R-R interval data to the external device 800 (step S6-4). The external device 800 performs processing of storing or displaying the data or transmitting the data to a server (step S6-10).

On the other hand, upon determining that the reliability is low, the biological information measurement apparatus 100 transmits the electrocardiogram waveform data to the external device 800 (step S6-5). The external device 800 analyzes the electrocardiogram waveform data and extracts R-R interval data (step S6-6). The external device 800 also analyzes the feature of the electrocardiogram waveform, optimizes the R-R interval data extraction algorithm in the biological information measurement apparatus 100 (step S6-7), and transmits algorithm change information to the biological information measurement apparatus 100 (step S6-8). The biological information measurement apparatus 100 receives the algorithm change information by the algorithm change information reception unit 600, changes the R-R interval data extraction algorithm of a biological feature amount data extraction unit 220 based on the received algorithm change information (step S6-9), and reflects it on subsequent R-R interval data extraction.

As a method of changing the algorithm, for example, a plurality of R-R interval data extraction algorithms are stored in the biological feature amount data extraction unit 220 of the biological information measurement apparatus 100 in advance, the external device 800 determines which algorithm is appropriate, and a code to designate the algorithm is transmitted from the external device 800 to the biological information measurement apparatus 100. As the types of algorithms, for example, an algorithm configured to detect an R wave from the peak of the amplitude of an electrocardiogram waveform, an algorithm configured to detect an R wave from the peak of the derivative of an electrocardiogram waveform, and the like are stored and selected.

Parameters used in the R-R interval data extraction algorithm of the biological feature amount data extraction unit 220 may be optimized in the external device 800 and transmitted from the external device 800 to the biological information measurement apparatus 100. The parameters are a filter constant (a cutoff frequency, the order of an FIR filter, or the like) when performing digital filtering of the electrocardiogram waveform in the biological information measurement apparatus 100, an amplification factor used when amplifying an electrocardiogram waveform, a threshold used when detecting a peak from the amplitude of an electrocardiogram waveform and detecting an R wave, a threshold used when detecting a peak from the derivative of an electrocardiogram waveform and detecting an R wave, and the like.

A program code to detect an R wave may be generated by the external device 800, transmitted to the biological information measurement apparatus 100, and rewritten.

When the biological information measurement apparatus includes the R-R interval data extraction algorithm changing unit, the algorithm and the like can be changed based on the determination of the external device, and the R-R interval data extraction accuracy can be improved. Since cases in which biological waveform data with a large data amount needs to be transmitted from the biological information measurement apparatus to the external device decrease, an effect of reducing power consumption can be obtained.

As described above, in this embodiment, the reliability of biological feature amount data is determined, and data to be transmitted is selected based on the reliability determination result. It is therefore possible to perform an efficient operation of transmitting biological waveform data only when the reliability of biological feature amount data is low.

In addition, since the biological feature amount extraction algorithm is changed based on a designation from the external device, a great effect can be obtained that is reduction of an extraction failure or an extraction error of a biological feature amount data in the biological information measurement apparatus.

Note that in the above embodiments, a case in which the biological waveform data is an electrocardiogram waveform data has been described. However, the present invention is not limited to this. Various cases can be considered, including a case in which the biological waveform data is a brain wave, and the feature amount is the strength of an a wave, a case in which the biological waveform data is a body acceleration, and the feature amount is the number of steps or active mass, and a case in which the biological waveform data is the intensity of reflected return light of infrared light with which a living body is irradiated, and the feature amount is a bloodstream, a pulse rate, or oxygen saturation.

INDUSTRIAL APPLICABILITY

The present invention is usable for biological electrodes used to acquire a biological signal such as an electrocardiogram signal every day and a biological signal measurement system using the biological electrodes.

EXPLANATION OF THE REFERENCE NUMERALS AND SIGNS

1 . . . living body, 2 . . . clothing, 10 . . . biological signal measurement apparatus, 11 . . . biological signal measurement apparatus (clothing side), 12 . . . terminal connector, 13-1-13-4 . . . snap button, 14 . . . signal processing unit, 15 . . . signal analysis unit, 16 . . . wireless communication unit, 17 . . . power supply unit, 18 . . . storage unit, 20 . . . positive electrode, 21 . . . negative electrode, 22 . . . indifferent electrode, 23, 24, 25 . . . wire, 30 . . . belt-shaped structure, 31 . . . cross brace-shaped structure, 40 . . . portable terminal, 50 . . . public network (Internet), 60 . . . cloud server, 100 . . . biological information measurement apparatus, 200 . . . biological waveform data measurement unit, 210 . . . biological waveform data transmission unit, 220 . . . biological feature amount data extraction unit, 230 . . . biological feature amount data transmission unit, 300 . . . transmission data selection unit, 400 . . . sensor (reliability determination unit), 500 . . . transmission data designation information reception unit, 600 . . . algorithm change information reception unit, 700 . . . extraction algorithm changing unit, 800 . . . external device

The invention claimed is:

1. A biological signal measurement system comprising:
   biological electrodes for detecting biological electric signals derived from a living body;
   a biological signal measurement apparatus including:
   a first data generator generating first biological digital data by quantizing, based on a first sampling rate, a biological electrical signal detected by the biological electrodes,
   a second data generator generating second biological digital data by downsizing the first biological digital data to a data size corresponding to a second sampling rate which is lower than the first sampling rate,
   a third data generator generating first feature amount data extracted from the first biological digital data, and
   a wireless transmitter transmitting in real time one of the second biological digital data and the first feature amount data to a portable terminal based on transmission data designation information that designates data to be transmitted; and
   an external device configured to receive at least one of the first biological digital data and the first feature amount data from the biological signal measurement apparatus,
   wherein the biological electrical signal is an electrocardiogram signal,
   the first feature amount data is data including at least an R-R interval of the electrocardiogram signal,
   the second data generator and the third data generator both use, as input data, the first biological digital data generated by the first data generator, and output the second biological digital data and the first feature amount data, respectively, and
   the external device is configured to determine reliability of the R-R interval, and transmit to the wireless transmitter, transmission data designation information that designates the second biological digital data to be transmitted by the wireless transmitter when the reliability of the R-R interval is lower than a predetermined reference value, and transmission data designation information that designates the first feature amount data to be transmitted by the wireless transmitter when the reliability of the R-R interval is equal to or larger than the predetermined reference value.

2. The biological signal measurement system according to claim 1, further comprising a portable terminal including:
   a wireless receiver receiving the second biological digital data and the first feature amount data,
   a fourth data generator generating second feature amount data by performing statistical analysis of the first feature amount data, and
   a display displaying at least one of the second biological digital data and the second feature amount data.

3. The biological signal measurement system according to claim 2, further comprising a server, the server including
   a server receiver receiving at least one of the first feature amount data and the second feature amount data transmitted from the portable terminal, and
   an analyzer performing statistical analysis of biological information using at least one of the first feature amount data and the second feature amount data received by the server receiver,
   wherein the portable terminal further comprises a transmission device transmitting at least one of the first feature amount data and the second feature amount data to the server.

4. The biological signal measurement system according to claim 3, wherein the portable terminal transmits at least one of identification information of the living body and position information of the portable terminal to the server, and
   the server performs the statistical analysis using at least one of the identification information and the position information received from the portable terminal.

5. The biological signal measurement system according to claim 2, wherein the second feature amount data is data including one of a ratio of a low frequency spectrum component amount of a temporal fluctuation of the R-R interval to a high frequency spectrum component amount, a value obtained by dividing a standard deviation of R-R intervals by an average value of the R-R intervals, and a ratio of the number of R-R intervals for which a difference between two consecutive R-R intervals is not less than 50 msec to a predetermined number of R-R intervals.

6. The biological signal measurement system according to claim 1, wherein the first sampling rate is a value ranging from not less than 200 Hz to not more than 2,000 Hz, and the second sampling rate is a value ranging from not less than 100 Hz to not more than 500 Hz.

7. A biological signal measurement system comprising:
   biological electrodes for detecting biological electric signals derived from a living body; and
   a biological signal measurement apparatus including:
   a first data generator generating first biological digital data by quantizing, based on a first sampling rate, a biological electrical signal detected by the biological electrodes,
   a second data generator generating second biological digital data by downsizing the first biological digital data to a data size corresponding to a second sampling rate which is lower than the first sampling rate,
   a third data generator generating first feature amount data extracted from the first biological digital data,
   a wireless transmitter transmitting in real time one of the second biological digital data and the first feature amount data to a portable terminal based on transmission data designation information that designates data to be transmitted; and
   an external device configured to receive at least one of the first biological digital data and the first feature amount data from the biological signal measurement apparatus,
   a transmission data designation information receiver receiving transmission data designation information that designates data to be transmitted by the wireless transmitter, and
   a transmission data selector selecting, based on the transmission data designation information, the data to be transmitted by the wireless transmitter,
   wherein the biological electrical signal is an electrocardiogram signal,
   the first feature amount data is data including at least an R-R interval of the electrocardiogram signal,
   the second data generator and the third data generator use, as input data, the first biological digital data generated by the first data generator, and output the second biological digital data and the first feature amount data, respectively, and the data selected by the data selector includes at least one of the second biological digital data and the first feature amount data, and the external device is configured to determine reliability of the R-R interval, and transmit to the wireless transmitter, transmission data designation information that designates the second biological digital data to be transmitted by the wireless transmitter when the reliability of the R-R interval is lower than a predetermined reference value, and transmission data designation information that designates the first feature amount data to be transmitted by the wireless transmitter when the reliability of the R-R interval is equal to or larger than the predetermined reference value.

8. A biological information measurement system according to claim 7, wherein
the first data generator includes a biological waveform data measurement device measuring biological waveform data as the first biological digital data,
the third data generator includes a feature amount data extraction device extracting biological feature amount data, as the first biological feature amount data, from the biological waveform data in accordance with a predetermined extraction algorithm, and
the wireless transmitter includes a data transmission device transmitting in real time at least one of the biological waveform data and the biological feature amount data, the data transmission device using different data transmission intervals to transmit the biological waveform data and the biological feature amount data.

9. The biological information measurement system according to claim 8, wherein the transmission data selector selects the data to be transmitted based on the biological feature amount data.

10. The biological information measurement system according to claim 8, further comprising a sensor configured to detect a change in states,
wherein the transmission data selector selects the data to be transmitted based on a state of the sensor.

11. The biological information measurement system according to claim 8, further comprising a reliability determination device determining reliability of the biological feature amount data,
wherein the transmission data selector selects the data to be transmitted based on a determination result of the reliability determination device.

12. The biological information measurement system according to claim 8, further comprising a transmission data designation information receiver receiving transmission data designation information that designates the data to be transmitted by the data transmitter,
wherein the transmission data selector selects the data to be transmitted based on the transmission data designation information.

13. A biological signal measurement system according to claim 12,
wherein the external device further comprises a reliability determination device determining reliability of the biological feature amount data received from the biological signal measurement apparatus and biological feature amount data extracted from the biological waveform data received from the biological signal measurement apparatus, and
transmitting the transmission data designation information to the biological signal measurement apparatus based on a determination result of the reliability of the biological feature amount data, and
the transmission data selector selects data to be transmitted to the external device based on the transmission data designation information.

14. The biological information measurement system according to claim 8, further comprising:
an algorithm change information receiver receiving algorithm change information that changes the predetermined extraction algorithm; and
an algorithm changer instructing the feature amount data extraction device to change the predetermined extraction algorithm based on the algorithm change information.

15. The biological information measurement system according to claim 14, wherein the algorithm change information is information to instruct change of at least one of a type, a parameter, and a program code of the predetermined extraction algorithm.

* * * * *